United States Patent [19]  [11] 4,335,152
Klemarczyk et al. [45] * Jun. 15, 1982

[54] METHYL SUBSTITUTED NORBORNANE CARBOXALDEHYDES, ORGANOLEPTIC USES THEREOF AND PROCESS FOR PREPARING SAME

[75] Inventors: Philip T. Klemarczyk, Old Bridge; James M. Sanders, Eatontown; Manfred H. Vock, Locust; Joaquin F. Vinals, Red Bank; Frederick L. Schmitt, Holmdel; Edward J. Granda, Englishtown, all of N.J.

[73] Assignee: International Flavors & Fragrances Inc., New York, N.Y.

[*] Notice: The portion of the term of this patent subsequent to Apr. 27, 1999, has been disclaimed.

[21] Appl. No.: 220,646

[22] Filed: Dec. 29, 1980

Related U.S. Application Data

[62] Division of Ser. No. 152,187, May 22, 1980, Pat. No. 4,284,824.

[51] Int. Cl.³ .............................................. A23L 2/26
[52] U.S. Cl. .................................................. 426/538
[58] Field of Search .................... 252/522 R; 568/445; 426/538

[56] References Cited

U.S. PATENT DOCUMENTS 1,944,732 1/1934 Diels et al. ....................... 568/445 X
2,373,568 4/1945 Joy et al. ......................... 252/522 X

OTHER PUBLICATIONS

Mehtiev et al., Chemical Abstracts, vol. 85, (1976), 192221x.

*Primary Examiner*—Bernard Helfin
*Attorney, Agent, or Firm*—Arthur L. Liberman

[57] ABSTRACT

Described are methyl-substituted norbornane carboxaldehyde having the generic structure:

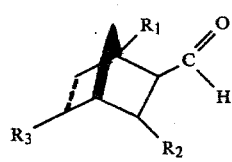

wherein the dashed line is a carbon-carbon single bond, or a carbon-carbon double bond, and $R_1$ $R_2$ and $R_3$ each represent methyl or hydrogen with the proviso that (i) $R_1$ is hydrogen when $R_3$ is methyl and (ii) $R_1$ is methyl when $R_3$ is hydrogen.

Also described are processes and compositions for augmenting or enhancing the flavor and/or aroma of consumable materials including foodstuffs, chewing gums, medicinal products, toothpastes, chewing tobaccos, perfumes, colognes and perfumed articles such as solid or liquid anionic, cationic, nonionic or zwitterionic detergents or fabric softeners or fabric softener articles using as the essential ingredient at least one of the methyl substituted norbornane carboxaldehydes of our invention.

2 Claims, 17 Drawing Figures

GLC PROFILE FOR EXAMPLE I.

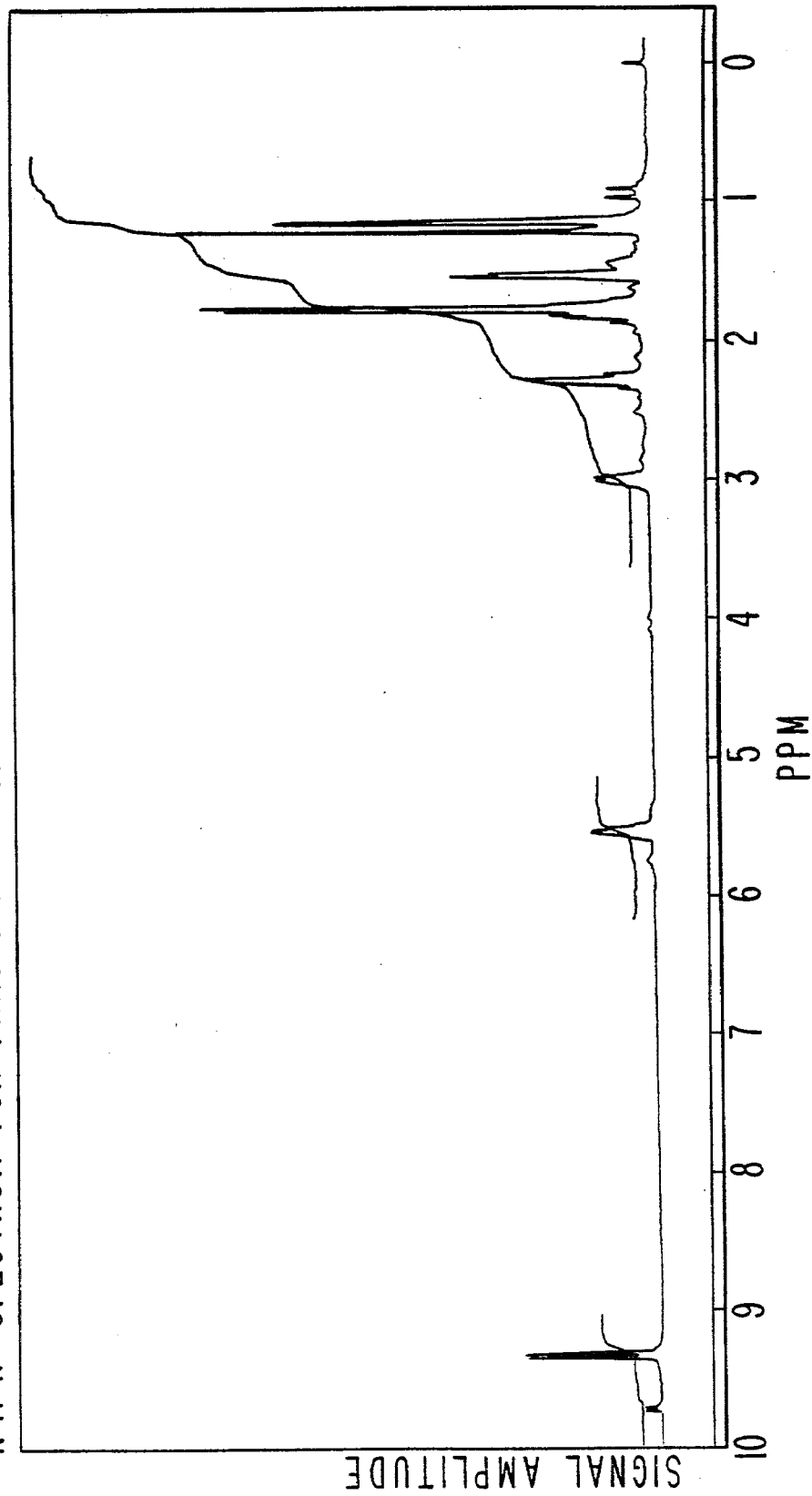

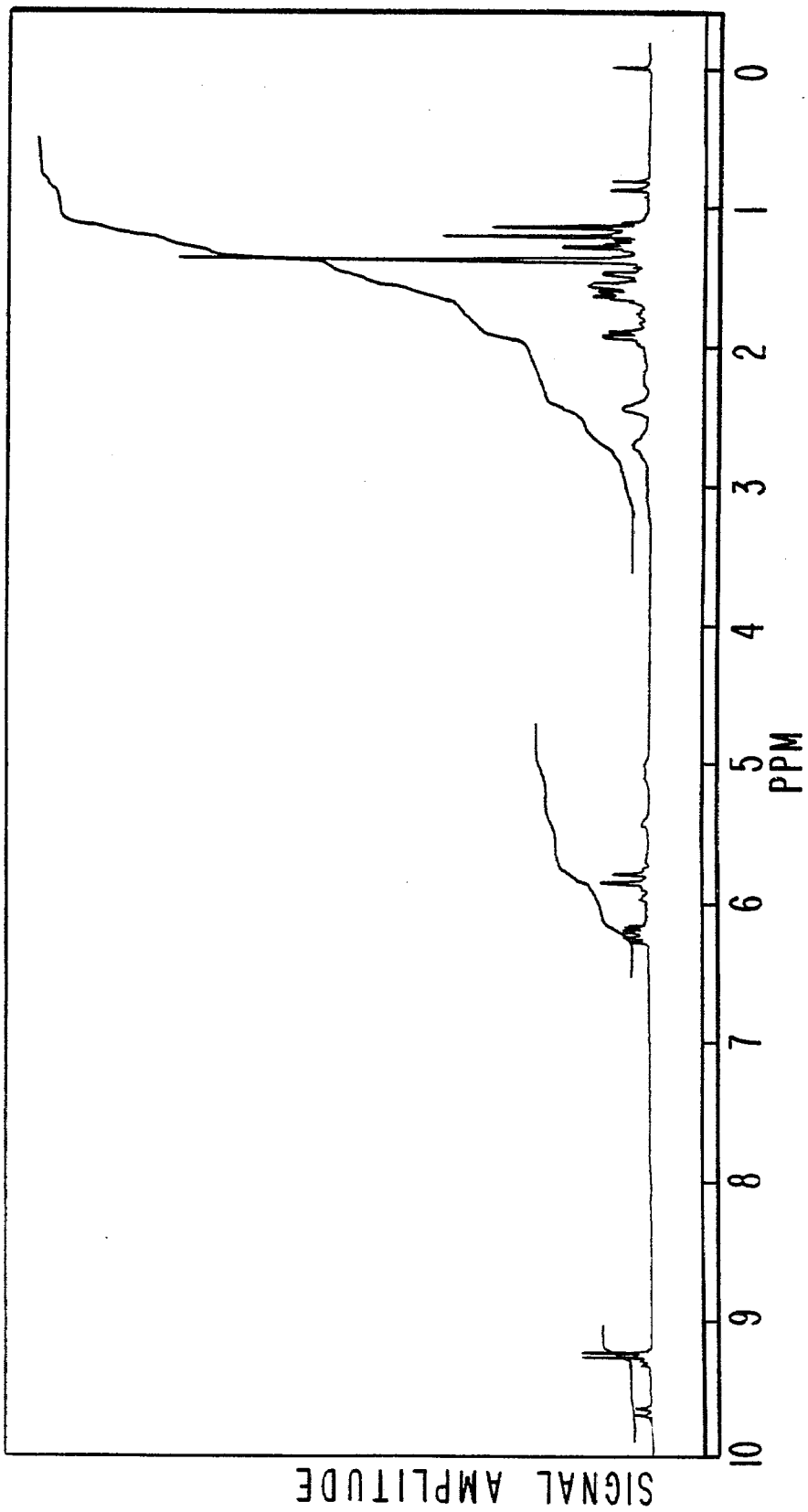

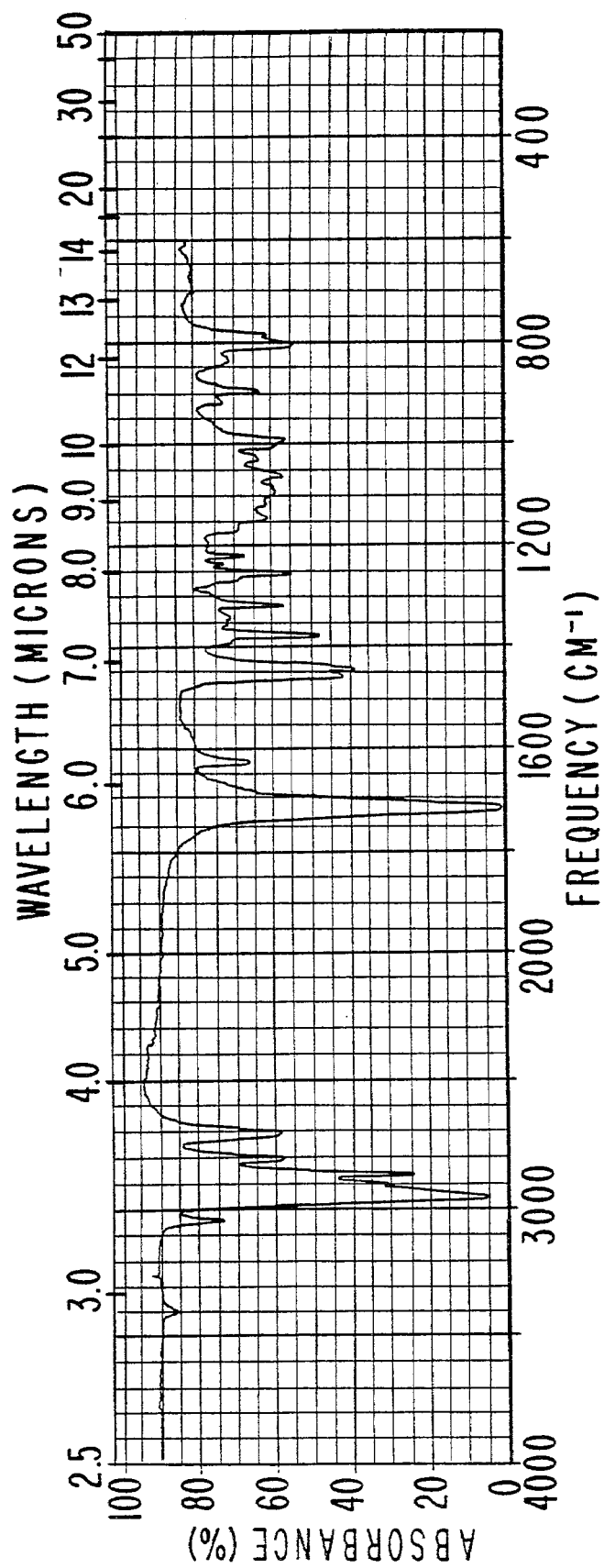

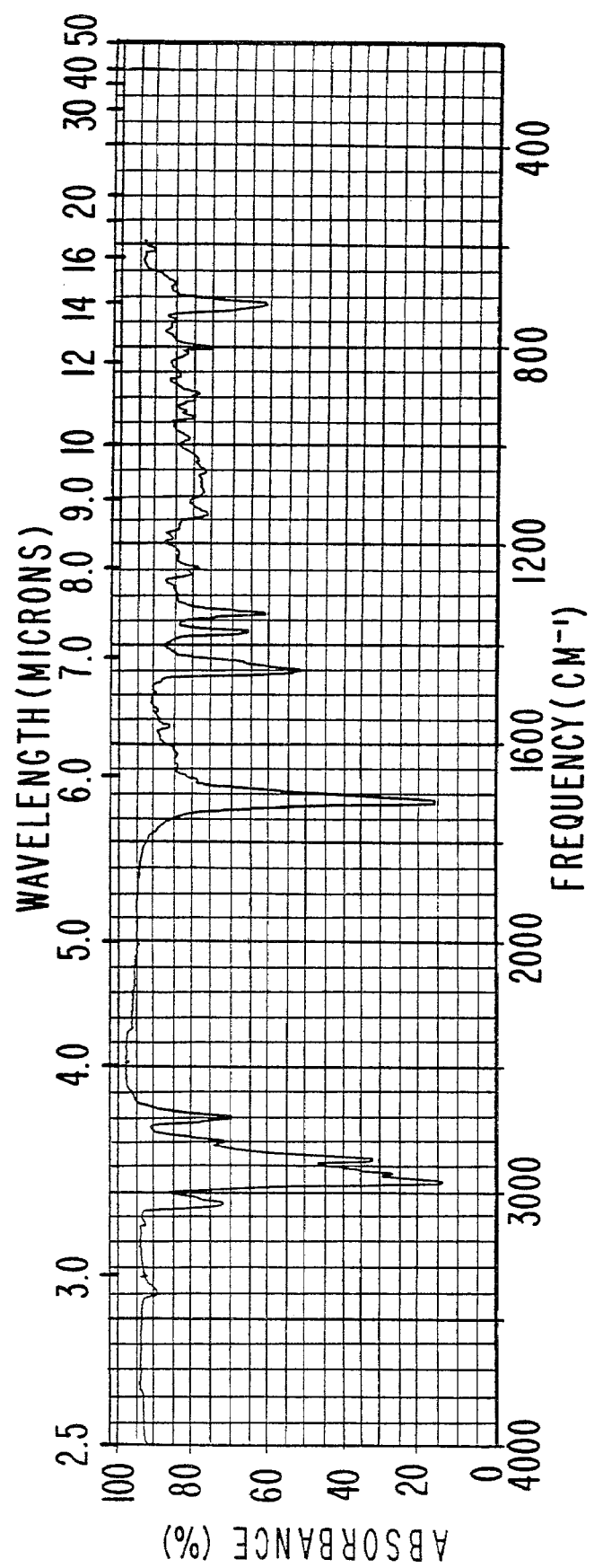

MASS SPECTRUM FOR EXAMPLE I.

GLC PROFILE FOR EXAMPLE II.

NMR SPECTRUM FOR PEAK 2 OF EXAMPLE II.

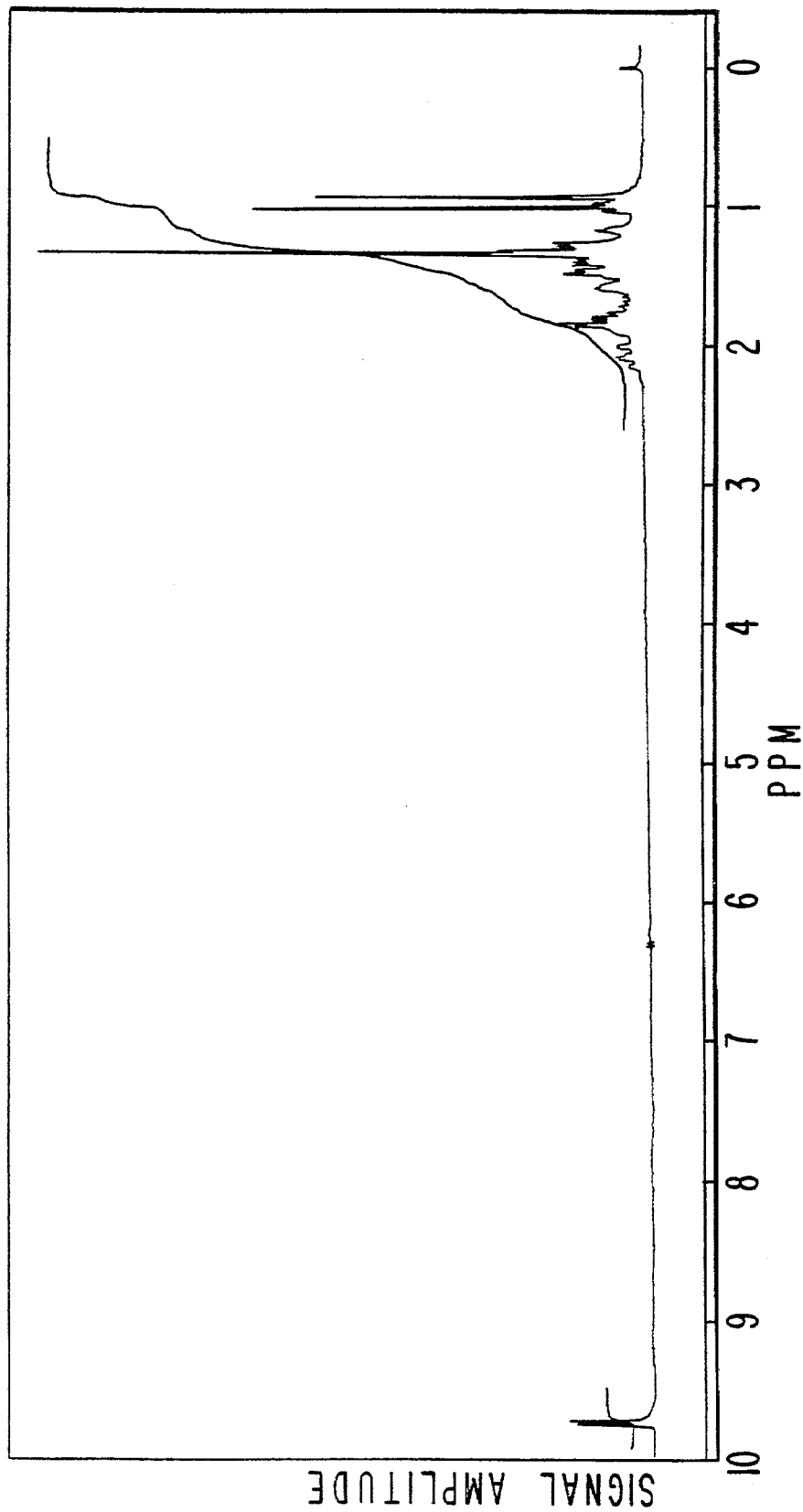

IR SPECTRUM FOR PEAK 2 OF EXAMPLE II.

IR SPECTRUM FOR PEAK I OF EXAMPLE II

MASS SPECTRUM
EXAMPLE II.

GLC PROFILE
EXAMPLE III.

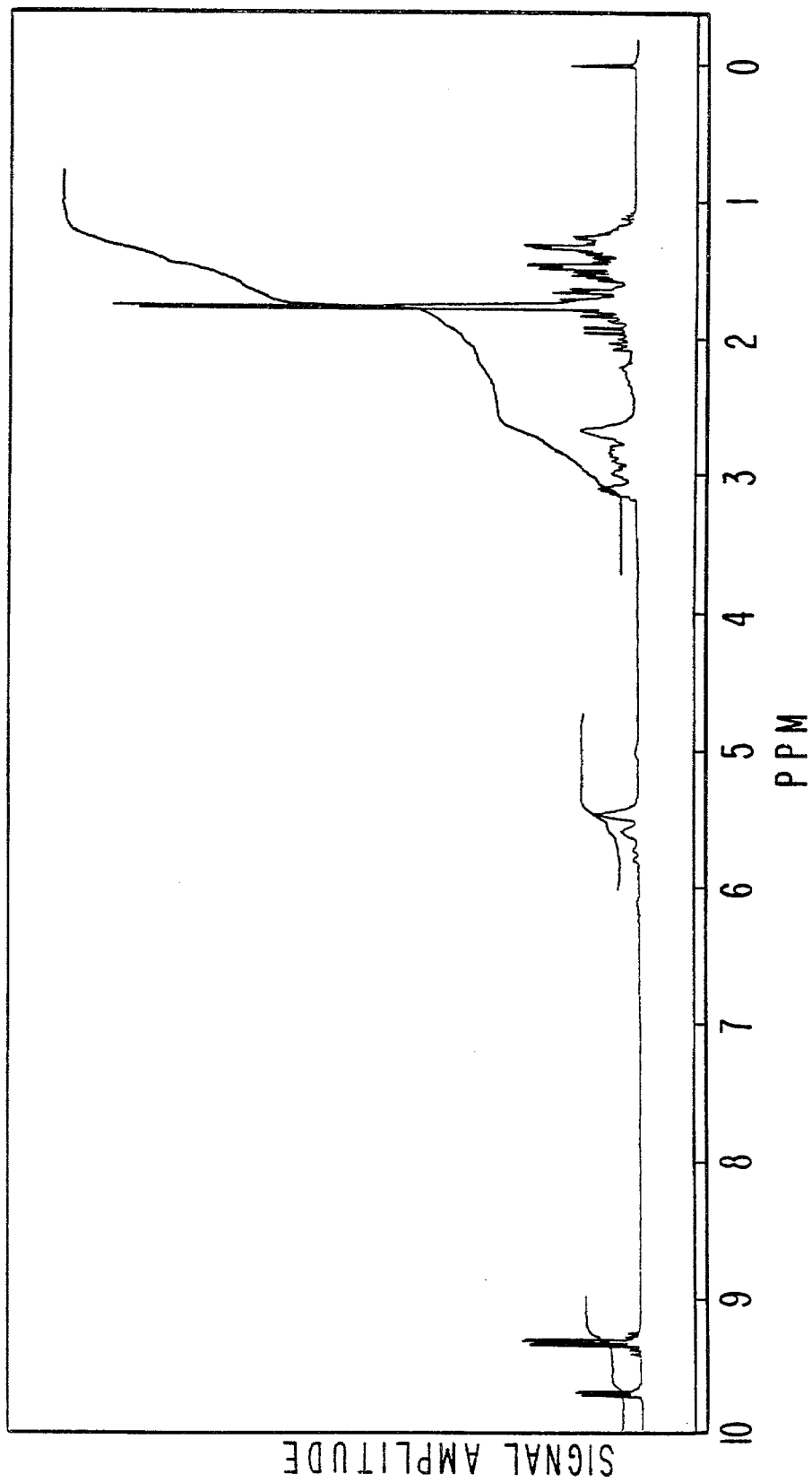

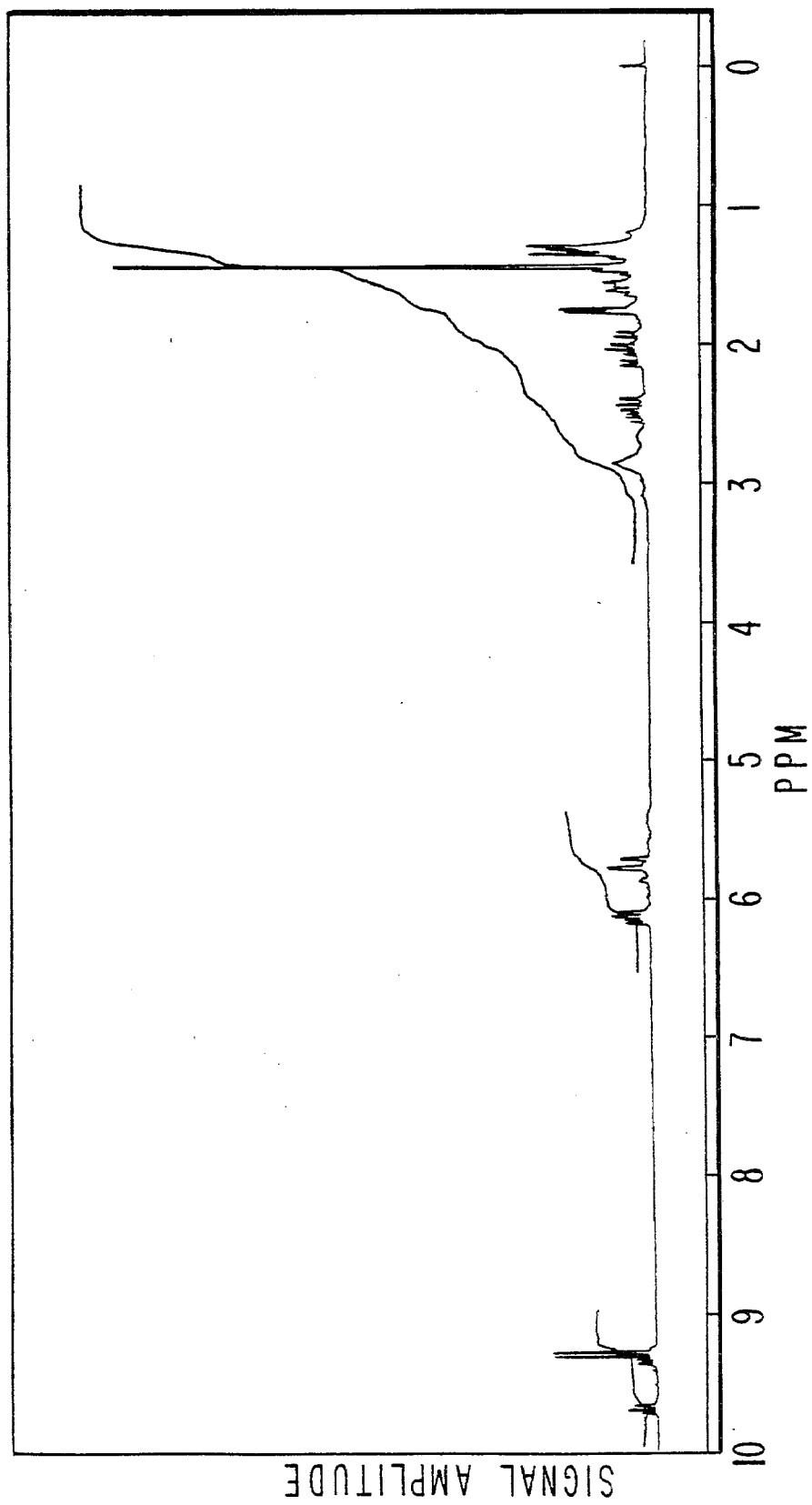

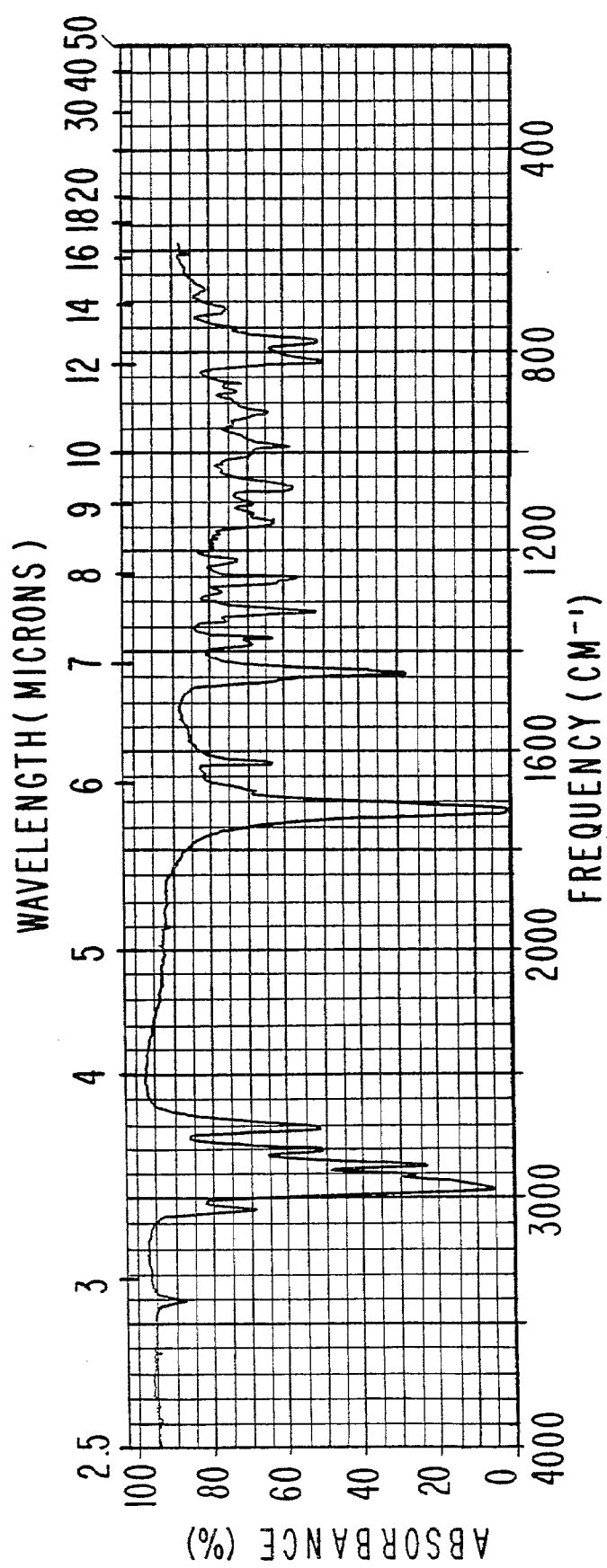

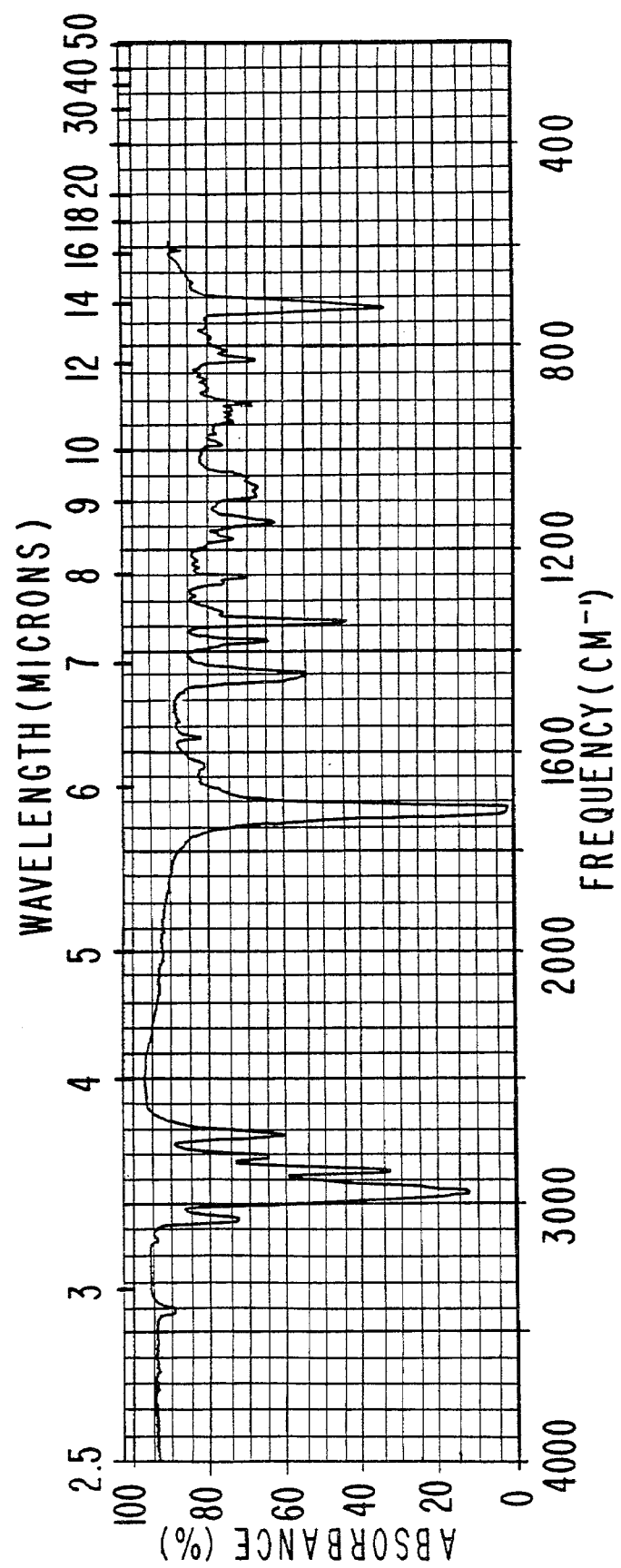

METHYL SUBSTITUTED NORBORNANE CARBOXALDEHYDES, ORGANOLEPTIC USES THEREOF AND PROCESS FOR PREPARING SAME

This is a divisional of application Ser. No. 152,187, filed May 22, 1980 and now U.S. Pat. No. 4,284,824.

BACKGROUND OF THE INVENTION

The invention provides novel methyl substituted norbornane carboxaldehydes having the generic structure:

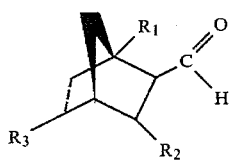

wherein the dashed line is a carbon-carbon single bond or a carbon-carbon double bond, and $R_1$, $R_2$ and $R_3$ represent methyl or hydrogen with the proviso that (i) $R_1$ is hydrogen when $R_3$ is methyl and (ii) $R_1$ is methyl when $R_3$ is hydrogen and uses thereof for their organoleptic properties in the consumable materials.

Materials which can provide green, cut grass-like and minty aromas with fruity (apple) and herbaceous undertones are known in the art of perfumery. Many of the natural substances which provide such fragrances and contribute the desired nuances to perfumery compositions are high in cost, vary in quality from one batch to another and/or are generally subject to the usual variations of natural products.

By the same token, materials which can provide eucalyptus-like, camphoraceous, blueberry-like, patchouli-like and fruity aroma nuances and camphoraceous, blueberry-like, patchouli-like flavor nuances are well known in the art of flavoring for foodstuffs, toothpastes, chewing gums and medicinal products. Many of the natural materials which provide such flavor notes and contribute desired nuances to flavor and to compositions are high in cost, vary in quality from one batch to another and/or are generally subject to the usual variations of natural products.

There is accordingly, a continuing effort to find synthetic materials which will replace, enhance or augment the essential flavor and fragrance notes provided by natural essential oils or compositions thereof. Unfortunately, many of these synthetic materials have the desired nuances only to a relatively small degree or else contribute undesirable or unwanted odor to the compositions. The search for materials which can provide a more refined blueberry flavor or raspberry flavor, for example, has been difficult and relatively costly in the areas of both natural products and synthetic products.

Artificial flavoring agents for foodstuffs have received increasing attention in recent years. For many years such food flavoring agents have been preferred over natural flavoring agents at least in part due to their diminished cost and their reproducible flavor qualities. For example, natural flavoring agents such as, extracts, concentrates and the like are often subject to wide variations due to changes in quality, type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, ice cream desserts and yogurt desserts and the like are apt to be stored prior to use.

The fundamental problem in creating artifical flavor agents is that the artificial flavor to be achieved be as natural as possible. This generally proves to be a difficult task since the negativism for flavor development in many foods, medicinal products, chewing gums and toothpastes is not completely known. This is noticeable in products having raspberry and blueberry flavor characteristics, particularly.

Even more desirable are products that can serve to substitute for difficult-to-obtain natural perfumery oils and at the same time substitute for natural flavoring agents in foodstuffs, chewing gums, medicinal products and toothpastes.

The prior art contains a large number of teachings wherein compounds having the aldehyde moiety or compounds having the norbornane moiety are useful in augmenting or enhancing the organoleptic properties of consumable materials. However, nothing in the prior art discloses the use for its organoleptic properties of any of the compounds defined according to the generic structure:

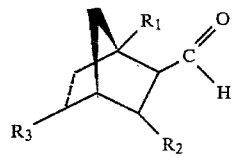

wherein $R_1$, $R_2$ and $R_3$ represent hydrogen or methyl and wherein the dashed line represents a single or double bond with the proviso that when $R_1$ is hydrogen, $R_3$ is methyl, and that when $R_1$ is methyl, $R_3$ is hydrogen. The prior art does show a compound having a similar but patentably distinct structure as an intermediate for producing compounds having organoleptic properties useful in augmenting or enhancing the aroma or taste of comsumable materials. Thus, U.S. Pat. No. 4,143,074 in Example I discloses the use as an intermediate in preparing alcohols and ketones, the compound having the structure:

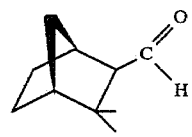

This compound is different in kind, in structure and in properties from the compounds defined according to the generic structure:

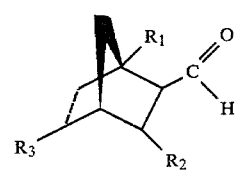

wherein the dashed line represents a carbon-carbon single bond or a carbon-carbon double bond and $R_1$, $R_2$ and $R_3$ represent hydrogen or methyl with a proviso that $R_1$ is hydrogen when $R_3$ is methyl and $R_1$ is methyl when $R_3$ is hydrogen.

U.S. Pat. No. 3,067,244 issued on Dec. 4, 1962 discloses interalia Diels-Alder reaction products of conjugated dienes including cyclopentadiene (at Column 1 line 64 with alpha, beta unsaturated alkanols at (Column 2 line 15) having the structure:

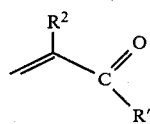

wherein $R^1$ represents one of hydrogen, hydroxyl or alkyl and $R^2$ represents hydrogen, carboxcyclic acid or alkyl. Included in the large list of unsaturated alkanols is acrolein at Column 2 line 42. Disclosed also in U.S. Pat. No. 3,067,244 is the process involving reaction of the conjugated diene and dienophile using Lewis acids including aluminum diethylchloride and aluminum ethyl dichloride but also including other Lewis acids, titanium tetrachloride, stannic chloride, aluminum trichloride, ferric chloride, zinc chloride and boron trifluoride. The reaction involving methyl cyclopentadienes and unsaturated dienophiles such as acrolein and crotonaldehyde, however, is not disclosed in U.S. Pat. No. 3,067,244 nor are the unobvious, unexpected and advantageous organoleptic properties of the resultant product suggested in U.S. Pat. No. 3,067,244. Indeed, there is no suggestion that in the reaction of the methylcyclopentadienes and the unsaturated alkanols of our invention only ethyl aluminum dichloride and aluminum diethyl chloride and their corresponding bromides will be usable as catalysts for the reaction, the other "catalysts" listed at lines 51–55 of Column 2 of U.S. Pat. No. 3,067,244 not being workable for the reaction of our invention. Indeed, in a paper published at Page 249 of the Jan. 5, 1961 issued of the Journal of the American Chemical Society entitled "Catalysts of the Diels-Alder Reaction+ by Fray & Robinson, the inventors on 3,067,244, it was further mentioned that "In comparative experiments with methylvinylketone and titamium tetrachloride . . . cyclopentadiene yielded only polymer and dimer respectively . . . "

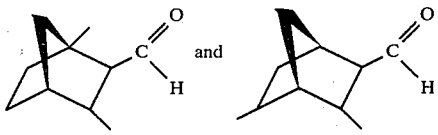

FIG. 2A represents the NMR spectrum for fraction 19 of the distillation product of the reaction of Example I consisting of the compound having the structure:

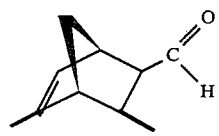

FIG. 2B represents the NMR spectrum for fraction 3 of the distillation product of the reaction product of Example I containing the compound having the structure:

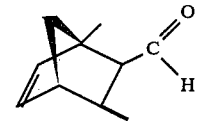

FIG. 3A represents the infra-red spectrum of Fraction 19 of the distillation product of the reaction product of Example I consisting of the compound having the structure:

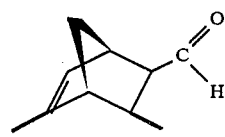

FIG. 3B represents the infra-red spectrum of Fraction 3 of the distillation product of the reaction product of Example consisting of the compound having the structure:

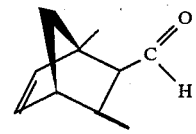

Figure 4:
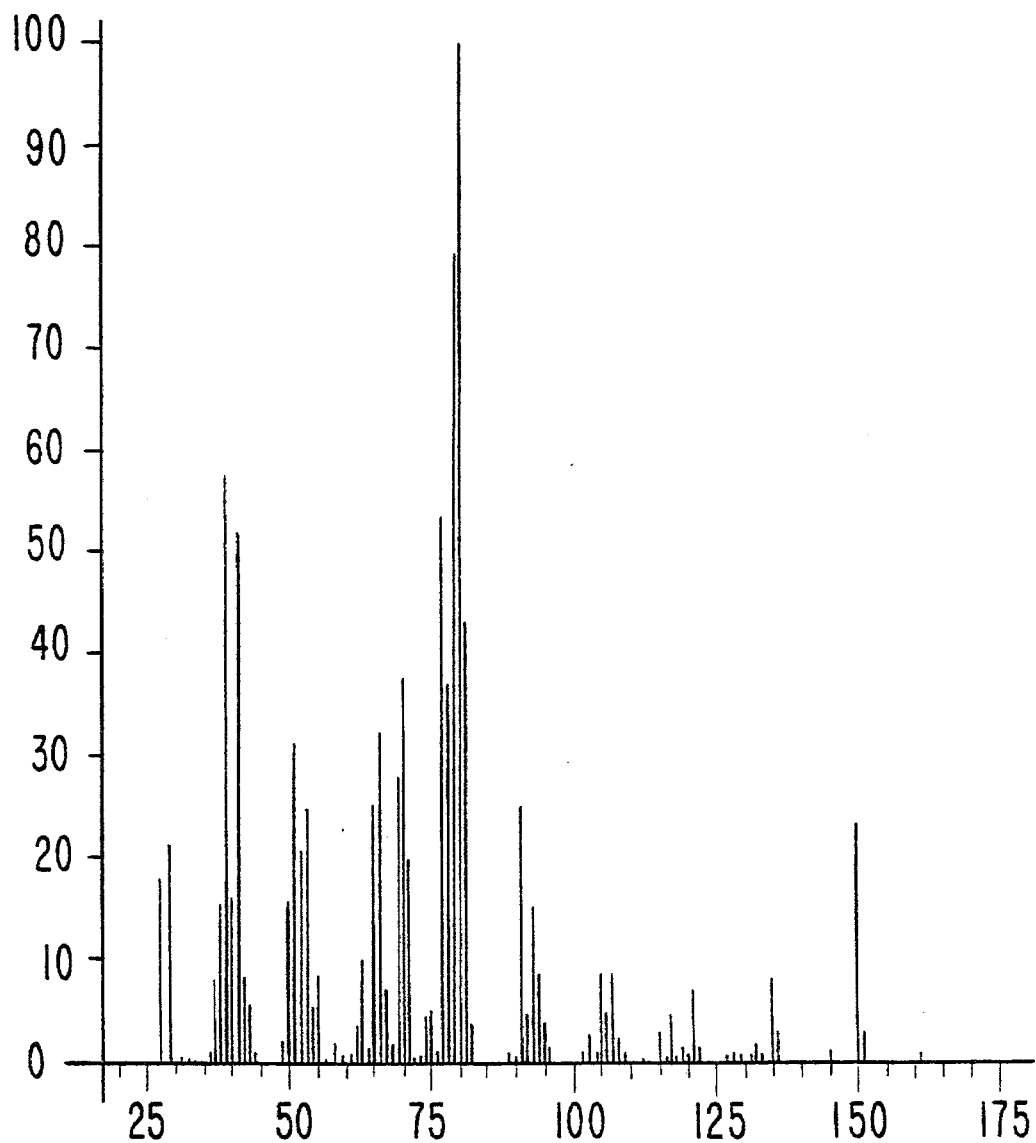

FIG. 4 represents the mass spectrum of the reaction product of Example I having the structures:

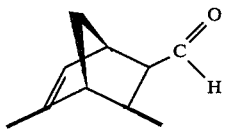

Figure 5:
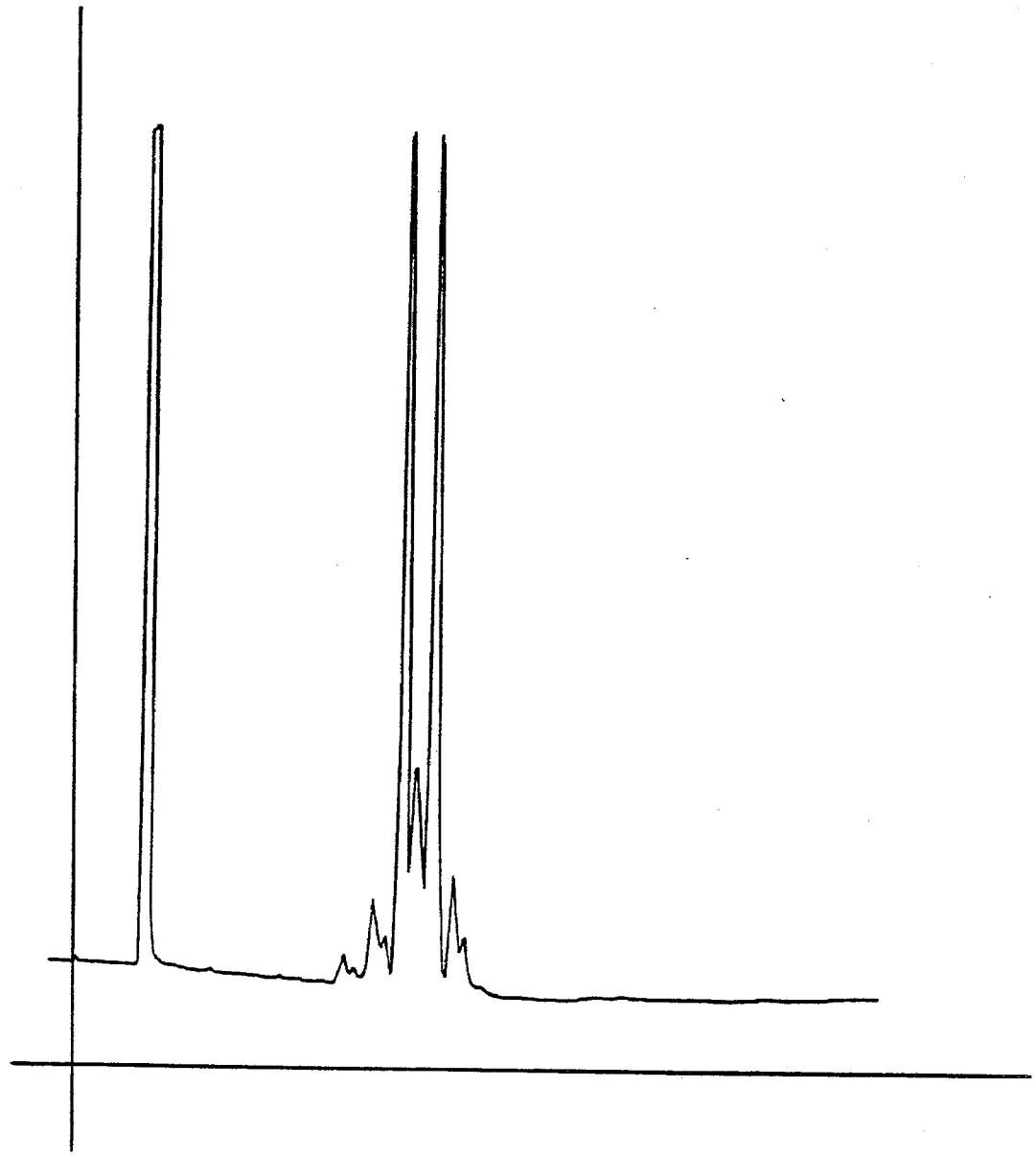
Figure 6A:
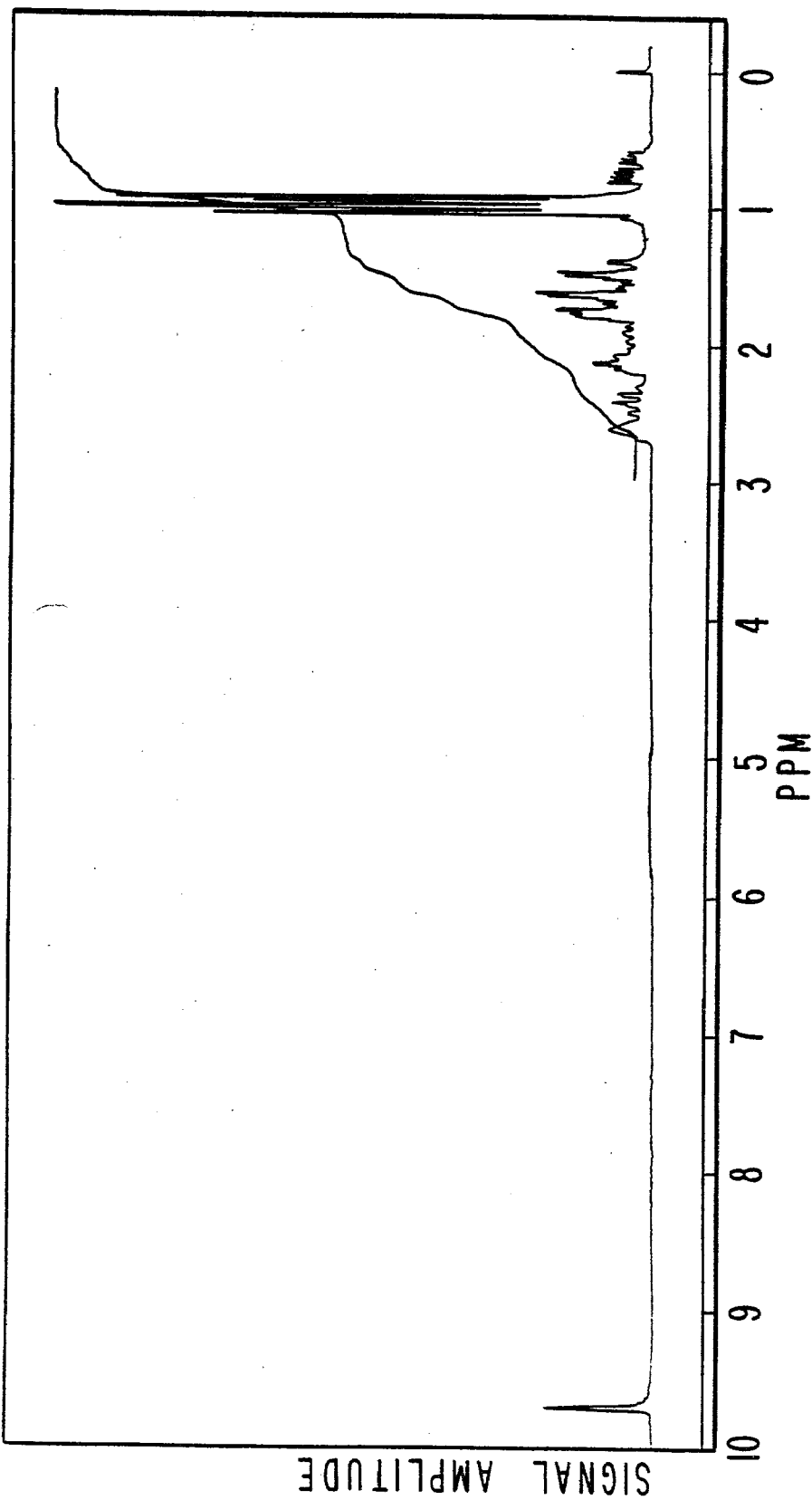

FIG. 5 represents the GLC profile of the crude reaction product solution of Example II containing the compounds having the structures:

FIG. 6A represents the NMR spectrum of peak 2 of the GLC profile of the reaction product of Example II containing the compound having the structure:

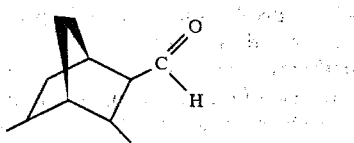

FIG. 6B represents the NMR spectrum for Peak 1 of the GLC profile of the reaction product of Example II consisting of the compound having the structure:

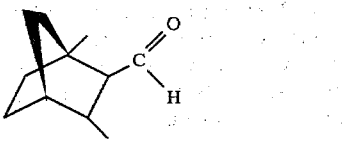

Figure 7A:
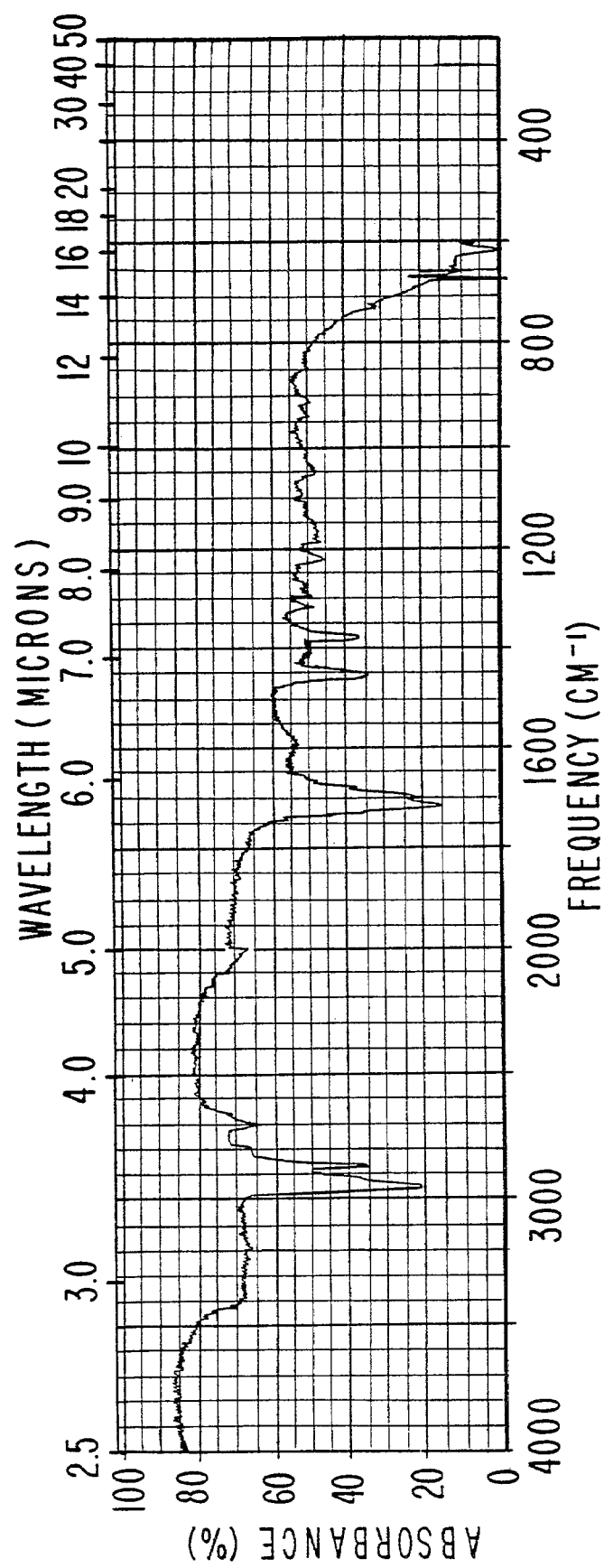

FIG. 7A represents the infra-red spectrum for Peak 2 of the GLC profile of the reaction product of Example II consisting of the compound having the structure:

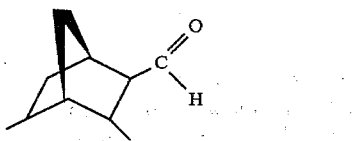

Figure 7B:
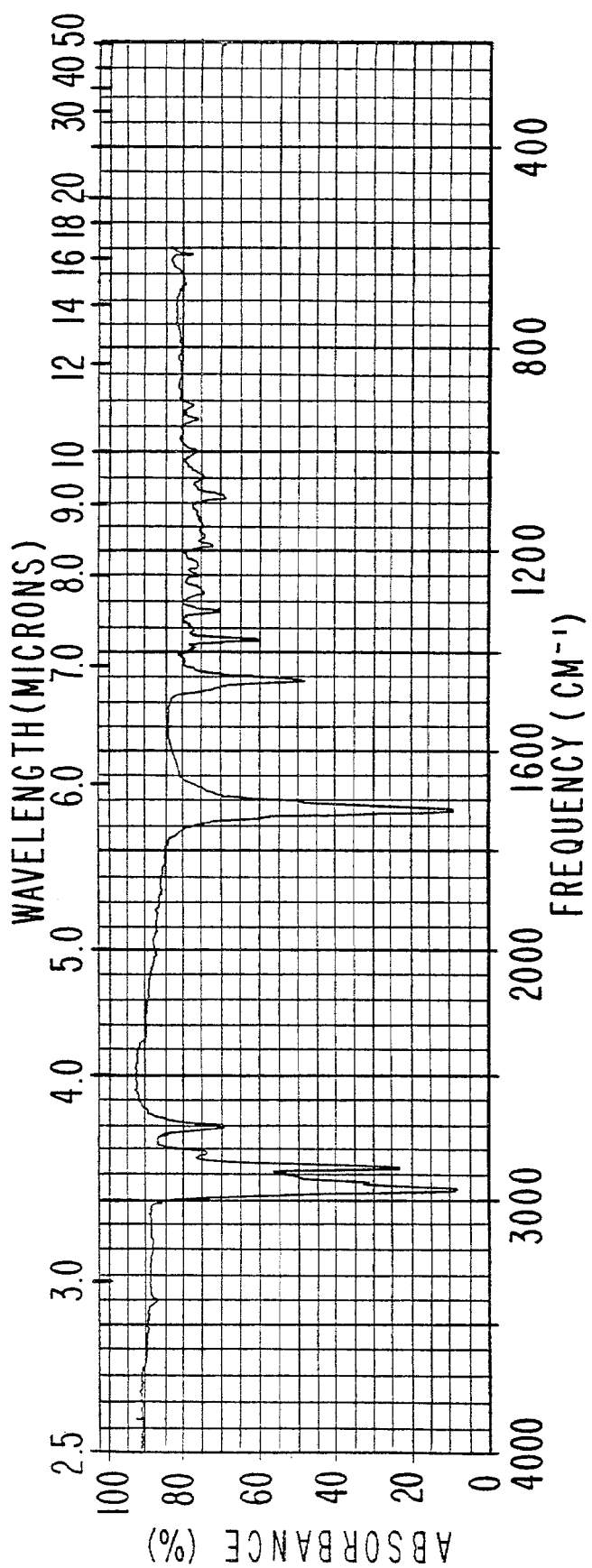

FIG. 7B represents the infra-red spectrum for Peak 1 of the GLC profile of the reaction product of Example II consisting of the compound having the structure:

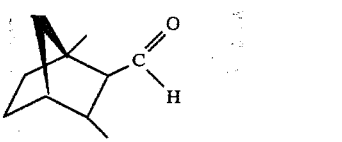

Figure 8:
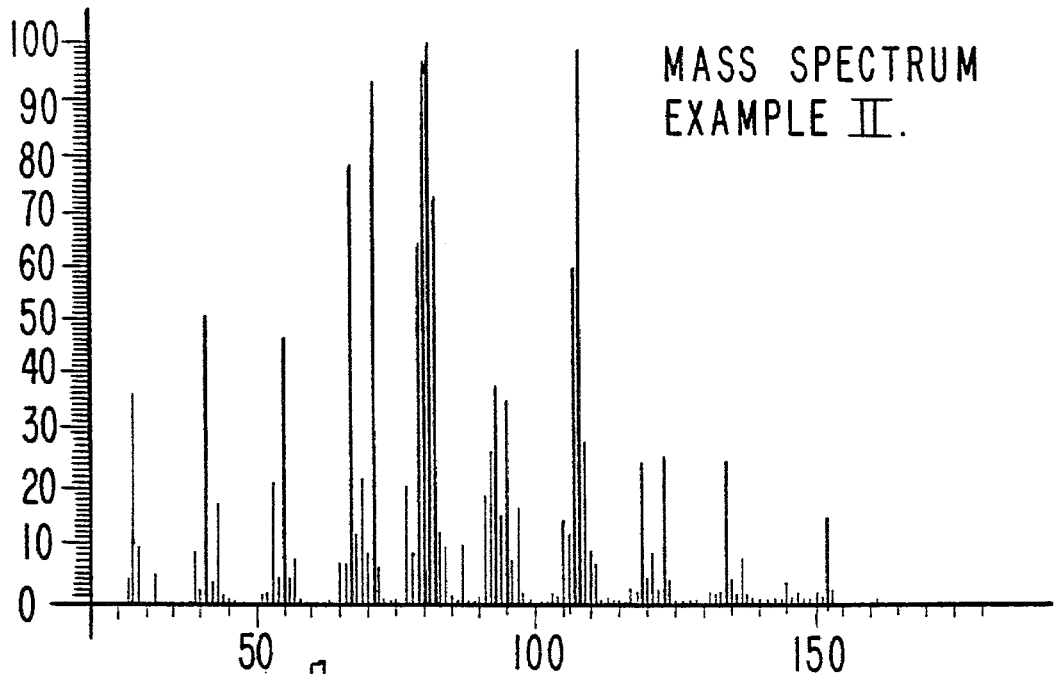

FIG. 8 represents the mass spectrum of the reaction product of Example II containing the compounds having the structures:

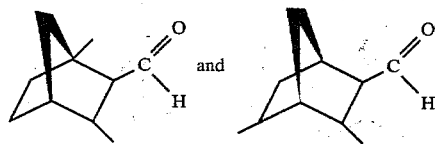

Figure 9:
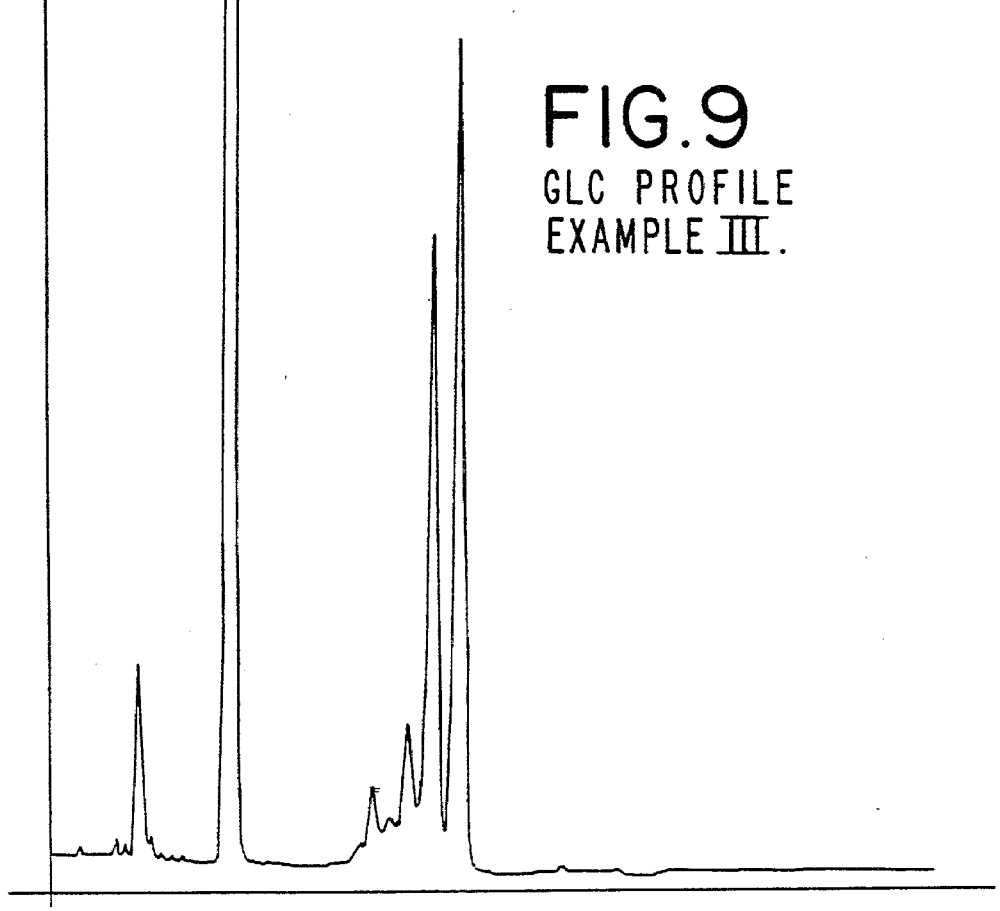

FIG. 9 represents the GLC profile of the reaction product after one hour of reaction of Example III containing the compounds having the structures:

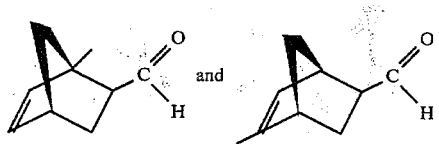

FIG. 10A represents the NMR spectrum for fraction 10 of the distillation product of the reaction product of Example III consisting of the compound having the structure:

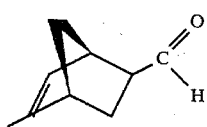

FIG. 10B represents the NMR spectrum for fraction 3 of the distillation product of the reaction product of Example III consisting of the compound having the structure:

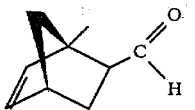

FIG. 11A represents the infra-red spectrum of fraction 10 of the distillation product of the reaction product of Example III consisting of the compound having the structure:

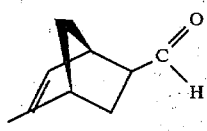

FIG. 11B represents the infra-red spectrum for fraction 3 of the distillation product of the reaction product of Example III consisting of the compound having the structure:

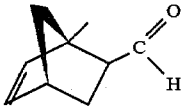

THE INVENTION

The present invention provides the compounds defined according to the generic structure:

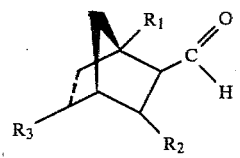

wherein the dashed line represents either a carbon-carbon single bond or a carbon-carbon double bond and $R_1$, $R_2$ and $R_3$ represent hydrogen or methyl with the proviso that when $R_1$ is hydrogen, $R_3$ is methyl and when $R_1$ is methyl, $R_3$ is hydrogen.

The present invention also provides an economical efficient process for synthesizing the compounds having the generic structure:

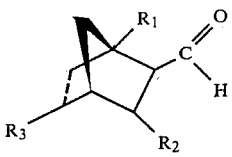

by reacting an unsaturated aldehyde, either an acrolein or crotonaldehyde with a mixture of 1-methyl-1,3-cyclopentadiene and 2-methyl-1,3-cyclopentadiene freshly produced from the process of cracking methylcyclopentadiene dimer.

The present invention also provides processes for using the compounds having the generic structure:

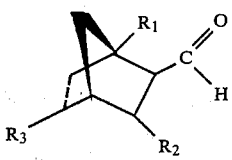

for their organoleptic properties in augmenting or enhancing the organoleptic properties of consumable materials, that is the aroma or taste of perfumes, colognes, perfumed articles (such as solid or liquid cationic, anionic, nonionic or zwitterionic detergents, soaps, fabric softener compositions, dryer-added fabric softener articles such as "BOUNCE" ®, a registered trademark of the Procter and Gamble Company of Cinncinatti, Ohio, fabric brighteners, and cosmetic powders), food flavor compositions, foodstuffs, chewing gums, toothpastes, chewing tobaccos and medicinal products particularly those having bluberry flavors or raspberry flavors.

The substituted norbornane carboxaldehydes of our invention may be prepared by first reacting an unsaturated aldehyde having the generic structure:

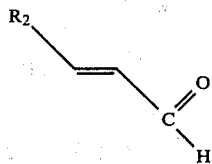

wherein $R_2$ is hydrogen or methyl and wherein when $R_2$ is methyl the foregoing structure represents cis or trans or mixtures of cis and trans isomers with 1-methyl-1,3-cyclopentadiene having the structure:

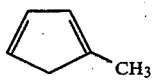

or a mixture of 1- and 2-methyl-1,3-cyclopentadiene signified by the structure:

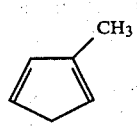

which are all freshly prepared from cracking methylcyclopentadiene dimer by passing the methylcyclopentadiene dimer through a distillation column at 175° C. which distillation column is packed preferably with Berle Saddles or Raschig Rings. The reaction of the methylcyclopentadiene(s) with the unsaturated aldehyde takes place at a temperature of between 0° and 50° C. in the presence of an alkyl aluminum halide catalyst having the structure:

wherein $R'$ is $C_1$–$C_3$-alkyl, preferably ethyl; X is chloro or bromo; $m+n=3$ with m being 1 when n is 2 and m being 2 when n is 1, the reaction preferably takes place in the presence of a solvent such as toluene, and in the presence of a promoter such as triethanolamine. The products of the reaction are compounds having the generic structures:

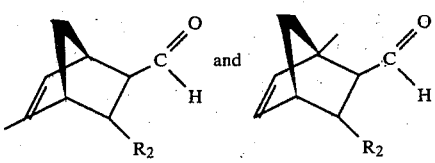

wherein $R_2$ is methyl or ethyl. The resulting products can be used in admixture for their organoleptic properties; or they can be separated as by fractional distillation to yield pure materials which can be used for their organoleptic properties; or the mixture can be used for further reaction with hydrogen to form the mixture of compounds having the structures:

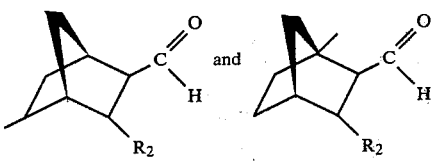

or the separated compounds may be individually hydrogenated to form the corresponding hydrogenated materials having the structures:

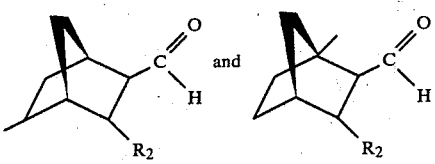

When the compounds having the structures:

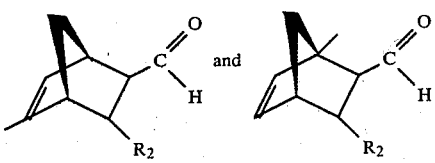

are hydrogenated, it is preferable to carry out the hydrogenation at a pressure between 25 psig and 100 psig, with a pressure of about 50 psig being most preferable. It is also preferred to carry out the hydrogenation at a temperature of between about 15° C. and about 50° C., with ambient temperatures, e.g. 25°–30° C. being most preferable. Furthermore, the time of reaction is a function of the maximum amount of hydrogen absorption taking place thus, when a hydrogen pressure of 50 psig is used and a temperature of 25° C. is used in the reaction, the time of maximum absorption is 5.5 hours.

The catalyst used in the hydrogenation may either be Rainey Nickel or a supported palladium catalyst such as, palladium-on-carbon or palladium-on-calcium carbonate. When the supported catalyst is used in the hydrogenation reaction, it is preferred to use from about 3% up to about 10% by weight palladium on support, preferably about 5% palladium on for example, carbon or calcium carbonate.

At the end of the reaction, the reaction product is fractionally distilled to yield fractions containing at least one compound generically defined according to the structure:

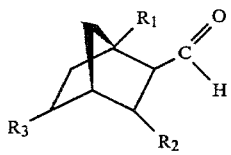

wherein one of $R_1$ or $R_3$ is methyl and the other is hydrogen, and wherein $R_2$ is methyl or hydrogen. These compounds can be further separated into their respective stereoisomers by reacting the corresponding aldehyde with a dextro- or laevo amine and then, either fractionally distilling or fractionally crystallizing the resultant stereoisomers followed by subsequent hydrolysis.

When the substituted norbornane carboxaldehyde derivatives of our invention are used as food flavor adjuvants, the nature of the co-ingredients included with the substituted norbornane carboxaldehyde derivatives of our invention used in formulating the product composition will also serve to alter, modify, augment or enhance the organoleptic characteristics of the ultimate foodstuff treated herewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic of note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended herein to mean a composition which comprises a substantially waterinsoluble, chewable plastic gum base such as chickle, or substitutes therefor, including jelutong, guttakay, rubber or certain cosmetible natural or synthetic resins or waxes. Incorporated with the gum base in admixture therewith may be plasticizers or softening agents, e.g., glycerine, and a flavoring composition which incorporates one or more of the substituted norbornane carboxaldehyde derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious, particularly from an organoleptic standpoint whereby the ultimate flavor and/or aroma of a consumable material used is not caused to have unacceptable aroma and taste nuances. Such materials may in general be characterized as flavoring agents or vehicles comprising broadly stabilizers, thickeners, surface agents, conditioners, other flavorants and flavor intensifiers.

Stabilizer compounds include preservatives, e.g. sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan; cellulose and cellulose derivatives such as carboxymethyl cellulose and methyl cellulose; natural and synthetic gums such as gum arabic, gum tragacanth, gelatin, proteinaceous materials, lipids, carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammomium bicarbonate, ammomium phosphate, citric acid, lactic acid, vinegar and the like, colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-cis-3-pentenoic acid; ketones and aldehydes, e.g., acetaldehyde, acetophenone, acetone, acetyl methyl carbinol, acrolein, n-butanal, crotonal, diacetyl, 2-methyl butanal, beta,-beta-dimethylacrolein, methyl-n-amyl ketone, n-hexanal, iso-pentanal, hydrocinnamic aldehyde, cis-3-hexenal, 2-heptanal, n-nonylaldehyde, 4-(p-hydroxyphenyl)-2-butanone, alpha-ionone, beta-ionone, methyl-3-butanone, benzaldehyde, β-damascone, β-damascenone, acetophone, 2-heptanone, o-hydroxyacetophone, 2-methyl-2-hepten-6-one, 2-octanone, 2-undecanone, 3-phenyl-4-pentenal, 2-phenyl-2-hexanal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, n-dodecane, methyl diphenyl, methyl naphthalene, mycrene, naphthalene, n-octadecane, n-tetradecane, tetramethyl naphthalene, n-tridecane, trimethyl naphthalene, undecane, caryophyllene, 1-phellandrene, p-cymene and 1-alpha-pimene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, 2-isopropyl-4,5-dimethylpyrazine, 1-methyl-2-ethylpyrazine, tetramethylpyrazine, trimethylpyrazine, essential oils, such as jasmine absolute, cassia oil, cinnamon barl oil, rose absolute, orris absolute, lemon essential oil, Bulgarian rose, yara yara and vanilla, lactones such as delta nonalactone, gamma nonalactone, delta dodecalactone, gamma dodecalactone, sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the substituted norbornane carboxaldehyde derivatives of our invention by not covering or spoiling the organoleptic properties (aroma and/or taste) thereof; (ii) be non-reactive with the substituted norbornane carboxaldehyde derivatives of our invention and (iii) be capable of providing an environment in which the substituted norbornane carboxaldehyde derivatives of our invention can be dispersed or admixed to provide a homogeneous medium. In addition, selection of one or more flavoring adjuvants, as well as the quantities thereof will depend upon the precise organoleptic character desired in the finished product. This, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the substituted norbornane derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavor composition.

The use of insufficient quantities of substituted norbornane carboxaldehyde derivatives will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of substituted norbornane carboxaldehyde derivatives ranging from a small but effective amount, e.g., 0.05 parts per million up to about 300 parts per million based on total composition are suitable. Concentrations in excess of the maximum quantity stated are not normally recommended, since they fail to provide commensurate enhancement of organoleptic properties. In those instances, wherein substituted norbornane carboxaldehyde derivatives are added to the foodstuff as an integral component of a flavoring composition, it is, of course, essential that the total quantity of flavoring composition employed be sufficient to yield an effective concentration of substituted norbornane carboxaldehyde derivatives in the foodstuff product.

Food flavoring compositions prepared in accordance with the present invention preferably contain substituted norbornane carboxaldehyde derivatives in concentrations ranging from about 0.1% up to about 15% by weight on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing substituted norbornane carboxaldehyde derivatives with, for example, gum arabic, gum tragacanth, carrageenan and the like, and thereafter spray-drying the resultant mixture whereby to obtain the particularate solid product. Pre-prepared flavor mixes in powder form, e.g., fruit flavored powder mixes are obtained by mixing the dried solid components e.g., starch, sugar and the like and one or more substituted norbornane carboxaldehyde derivatives in a dry blender until the requisite degree of uniformity is achieved.

It is presently preferred to combine with substituted norbornane carboxaldehyde derivatives of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Guaiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexanal;
2-Phenyl-2-pentenal;
3-Phenyl-4-pentenal diethyl acetal;
Beta-Damascone (1-crotonyl-2,6,6-trimethyl-cyclohex-1-ene);
Beta-Damascenone (1-crotonyl-2,6,6-trimethyl-cyclohexa-1,3-diene);
Beta-cyclohomocitral (2,6,6-trimethylcyclohex-1-ene carboxaldehyde)
Isoamyl butyrate;
Cis-3-hexanol-1;
2-Methyl-2-pentenoic acid;
Elemecine (4-allyl-1,2,6-trimethoxybenzene);
Isoelemecine (4-propenyl-1,2,6-trimethoxybenzene); and 2-(4-Hydroxy-4-methylpentyl) norbornadiene.

The methyl substituted norbornane carboxaldehyde derivatives of our invention can be used to contribute green, cut grass-like and minty aromas with fruity (apple) and herbaceous undertones to perfume compositions, perfumed articles such as solid or liquid anionic, cationic, nonionic or zwitterionic detergents, fabric softener compositions, fabric softener articles, fabric optical brighteners and other fabric conditioners. As olfactory agents the substituted norbornane carboxaldehyde derivatives of our invention can be formulated into or used as components of a "perfumed composition".

The term "perfumed composition" is used herein to mean a mixture of organic compounds including for example, alcohols, aldehydes (other than the aldehydes which are the methyl substituted norbornane carboxaldehyde derivatives of our invention) ketones, nitriles, ethers, lactones and frequently hydrocarbons which are admixed so that the combined odors of the individual components produced a pleasant or desired fragrance. Such perfumed compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the compositions.

The amount of methyl substituted norbornane carboxaldehydes of our invention which will be effective in perfume compositions depends upon many factors including the other ingredients, their amounts and the effects which are desired. It has been found that perfume compositions containing as little as 1% of the methyl substituted norbornane carboxaldehydes of our invention or even less and perfume compositions containing as much as 70% of the methyl substituted norbornane carboxaldehyde derivatives of our invention can be used to impart interesting green, cut grass-like and minty aromas with fruity (apple-like) and herbaceous undertones to perfumed articles, perfumed compositions and colognes. Such perfumed articles include fabric softener compositions, dryer-added fabric softeners, cosmetic powders, talcs and solid or liquid anionic, cationic, nonionic or zwitterionic detergents. The amount employed can range up to 70% and will depend on considerations of cost, nature of the end product and the effect desired on the finished product and particular fragrance sought.

Thus, the methyl substituted norbornane carboxaldehydes of our invention can be ised alone or in a perfumed composition as an olfactory component in solid or liquid anionic, cationic, nonionic or zwitterionic detergents (including soaps), space odorants and deodorants; perfumes; colognes, toilet waters, bath salts; hair preparations such as lacquers, brillantines, pomades and shampoos; cosmetic preparations such as creams, deodorants, hand lotions and sunscreens; powders such as talcs, dusting powders, face powder and the like. When used as an olfactory compotient of a perfumed article such as a solid or liquid cationic, nonionic, anionic or zwitterionic detergent or of a cosmetic powder, as little as 0.01% of one or more of the methyl substituted norbornane carboxaldehydes of our invention will suffice to provide an interesting green, cut grass-like and minty aroma with fruity (apple-like) and herbaceous undertones. Generally, no more than 0.8% of the methyl substituted norbornane carboxaldehyde derivatices of our invention is required.

In addition, the perfume compositions of our invention can contain a vehicle or carrier for the methyl substituted norbornane carboxaldehyde derivatives of our invention alone or wtih other ingredients. The vehicle can be a liquid such as an alcohol, such as ethanol, a glycol such as propylene glycol, or the like. The carrier can be an absorbent solid such as a gum, or components for encapsulating the composition as by coacervation.

The following Examples I-III set forth processes for preparing the methyl substituted norbornane carboxaldehyde derivatives of our invention as it is presently preferred to practice it and as embodied in the generically illustrated process:

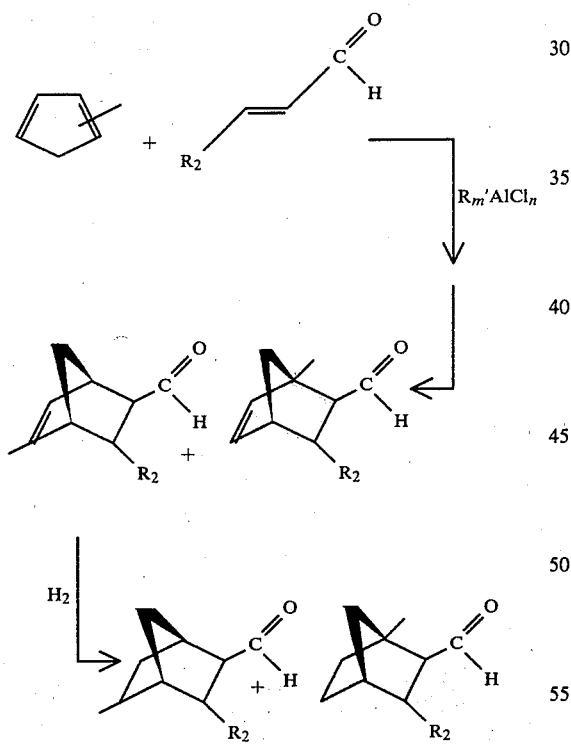

wherein $R_2$ is methyl or hydrogen, $R'$ is $C_1$-$C_3$ alkyl; with $m+n=3$, and $m=1$ or 2 and $n=1$ or 2. Example A represents a process for cracking methyl bicyclopentadiene to form the methyl cyclopentadiene precursors used in the process of our invention in Examples I and III. Examples IV et seq represent methods for using the methyl substituted norbornane carboxladehydes of our invention for their organoleptic properties. Unless otherwise indicated, all parts and percentages are by weight.

EXAMPLE A

Into a 2-liter distillation flask equipped with eighteen inch column and packed with Berle Saddles, a small Rushover Head, a nitrogen purge and a large receiver colled using an isopropyl alcohol flask dry-ice bath is placed, 10 grams of Primol ® and 1 kilogram of methylcyclopentadiene dimer.

The reaction mass is heated to 150° C. and the temperature is controlled with a "Thermowatch" ® (Registered trademark of Instruments for Research and Industry, of Cheltenham, Pa.), using a head thermometer. A mixture of 1-methyl-1,3-cyclopentadiene and 2-methyl-1,3-cyclopentadiene is collected in the receiver which is maintained at a temperature of −78° C. The product has a vapor temperature (head temperature) of 60° C. and a pot temperature of 173° C. Distillation is carried out until the head temperature reaches 82° C. and the pot temperature reaches 187° C., the distillation being carried out at atmospheric pressure.

EXAMPLE I

PREPARATION OF 1,3 AND 3,5-DIMETHYL-5-NORBORNENE CARBOXALDEHYDE REACTION

Reaction:

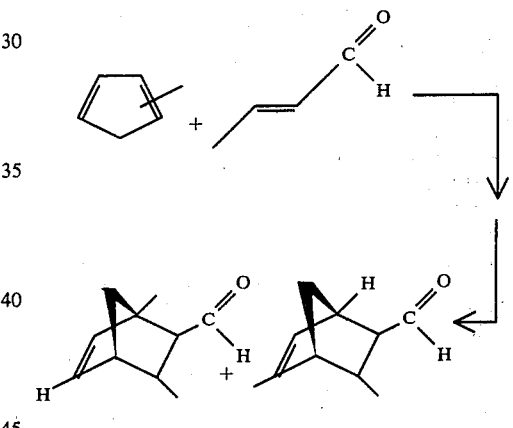

Into a 3 liter Morton Flask equipped with stirrer, thermometer, condenser, bidwell, trap, addition funnel, heating mantle and cooling bath is placed one liter of toluene and 500 grams of 85% crotonaldehyde. The resulting mixture is heated to reflux to remove the water and the resultant material is then cooled to 20°-25° C. over a period of 20 minutes while maintaining the mixture temperature at 23° C., 51 grams of ethyl aluminum dichloride is added. While maintaining the reaction temperature over a range of 22°-25° C. over a period of twenty minutes, 400 grams of a 50% solution of 1-methyl-1,3-cyclopentadiene and 2-methyl-1,3-cyclopentadiene (produced according to Example A) in toluene is added to the reaction mass. At the end of another twenty five minutes, while maintaining the reaction temperature at 22° C., GLC analysis indicates that the reaction is complete.

The reaction mass is then poured onto one liter of hydrochloric acid. The reaction mass now exists in two phases; an aqueous phase and an organic phase. The aqueous phase is extracted with 500 ml of toluene and the organic phase and toluene extracts are combined. The resulting organic material is washed as follows:

A—one 1-liter water portion
B—one 1-liter saturated sodium bicarbonate portion
C—two 1-liter portions of water and resulting mixture has a pH of 6. The solvent is then stripped off under vacuum and then fractionally distilled on a 12 in h Goodloe column yielding the following fractions:

| Fraction No. | Vapor Temp.(°C.) | Liquid Temp(°C.) | Pressure (mm Hg) | Reflux Ratio |
|---|---|---|---|---|
| 1 | 51/40 | 63/50 | 4.5/2.5 | 9.1 |
| 2 | 30 | 45 | 2.0 | 9.1 |
| 3 | 30 | 45 | 2.0 | 9.1 |
| 4 | 31 | 46 | 2.0 | 9.1 |
| 5 | 31 | 47 | 2.0 | 9.1 |
| 6 | 32 | 48 | 2.0 | 9.1 |
| 7 | 32 | 48 | 2.0 | 9.1 |
| 8 | 32 | 48 | 2.0 | 9.1 |
| 9 | 32 | 48 | 2.0 | 9.1 |
| 10 | 32 | 50 | 2.0 | 9.1 |
| 11 | 33 | 54 | 2.0 | 9.1 |
| 12 | 33 | 54 | 2.0 | 9.1 |
| 13 | 35/40 | 51/54 | 2.0/2.5 | 9.1 |
| 14 | 40 | 55 | 2.5 | 9.1 |
| 15 | 42 | 56 | 2.5 | 9.1 |
| 16 | 42 | 58 | 2.2 | 9.1 |
| 17 | 42 | 76 | 2.2 | 1.1 |
| 18 | 43 | 90 | 2.5 | 1.1 |
| 19 | 45 | 135 | 4.0 | 1.1 |

NMR, IR and mass spectral analysis yield the information that the resulting distillate consists of the compounds having the structures:

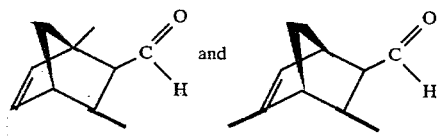

Figure 1:
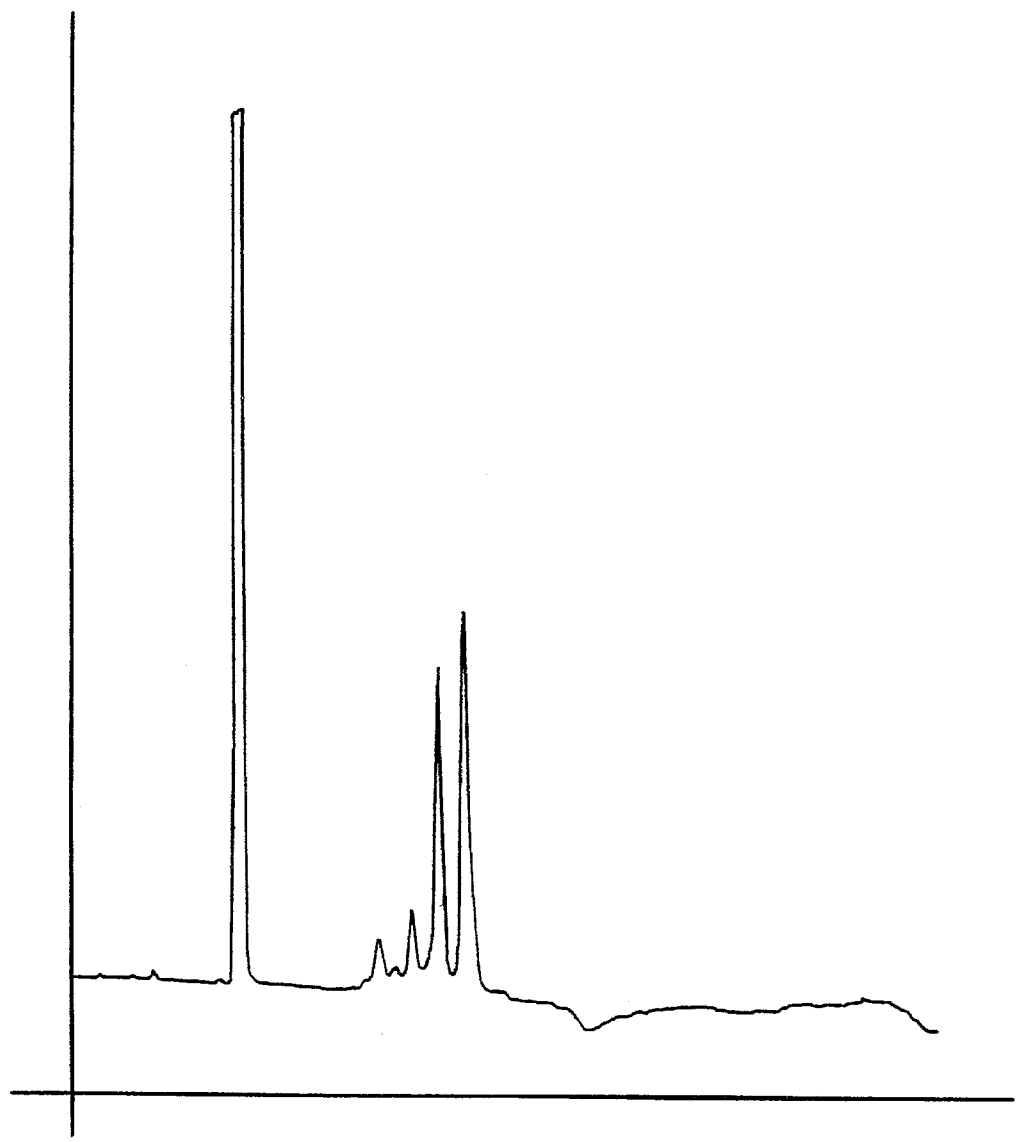
FIG. 1 sets forth the GLC profile at the end of thirty minutes of reaction of the reaction product of Example I containing the compounds having the structures.

FIG. 1 represents the GLC profile of the reaction product after thirty minutes of reaction.

FIG. 2A represents the NMR spectrum for fraction 19 of the foregoing distillation product of the reaction product of this example consisting of the compound having the structure:

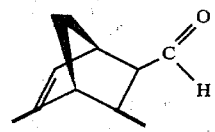

FIG. 2B represents the NMR spectrum for fraction 3 of the distillation product of the foregoing distillation consisting of the compound having the structure:

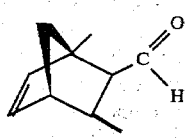

FIG. 3A represents the infra-red spectrum for fraction 19 of the foregoing distillation consisting of the compound having the structure:

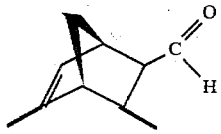

FIG. 3B represents the infra-red spectrum for fraction 3 of the foregoing distillation consisting of the compound having the structure:

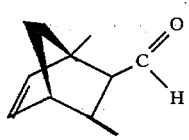

FIG. 4 represents the mass spectrum of the reaction product consisting of the compounds having the structures:

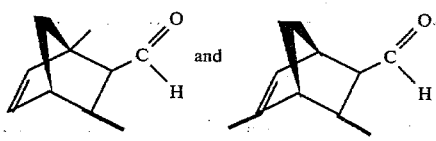

EXAMPLE II

PREPARATION OF 1,3- AND 3,5-DIMETHYL-5-NORBORNANE CARBOXALDEHYDE

Reaction:

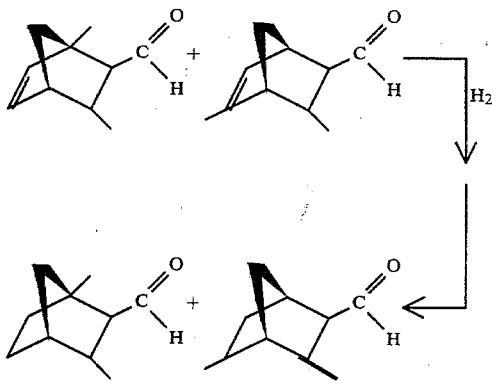

Into a 500 ml. pressure bottle on a Parr shaker is placed 150 grams of the mixture of 1,3- and 3,5-dimethyl-5-norbornane carboxaldehyde prepared according to Example I (Bulked fractions 1-19) and 100 ml. isopropyl alcohol and 1 gram of 5% (weight) palladium on carbon.

The 500 ml. pressure bottle is purged six times with hydrogen and then closed and pressurized to 50 lbs./psig with hydrogen. Reaction is continued while maintaining the pressure at 50 psig until hydrogen absorption ceases (5.5 hours). A total pressured drop of 71 psig of hydrogen is observed from the hydrogen reservoir. The resulting reaction mass is complete as shown by NMR analysis. The resulting solution is then filtered after opening the Parr shaker and pressure bottle. The solvent is stripped off and accrued material is distilled to yield 122 grams (80% theoretical yield) of a product consisting of compounds having the structures:

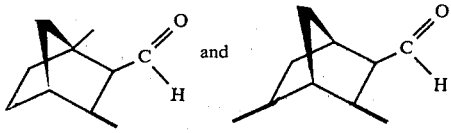

the resulting product is then distilled on a 3 foot spinning band column to yield the following fractions:

| Fraction No. | Vapor Temp. (°C.) | Liquid Temp (°C.) | Pressure (mm Hg) | Reflux Ratio |
|---|---|---|---|---|
| 1 | 50/54 | 60/61 | 4.0/4.0 | 18 |
| 2 | 54 | 64 | 5.0 | 20 |
| 3 | 56 | 65 | 5.0 | 24 |
| 4 | 56 | 66 | 5.0 | 22 |
| 5 | 57 | 68 | 6.0 | 21 |
| 6 | 58 | 93 | 6.0 | 17 |

FIG. 5 represents the GLC profile for the crude reaction mass.

FIG. 6A represents the NMR spectrum for peak 2 of the foregoing GLC profile consisting of the compound having the structure:

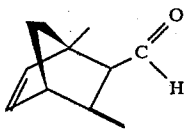

FIG. 6B represents the NMR spectrum for peak 1 of the foregoing GLC profile consisting of the compound having the structure:

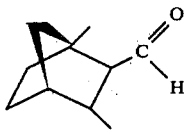

FIG. 7A represents the infra-red spectrum for peak 2 of the foregoing GLC profile consisting of the compound having the structure:

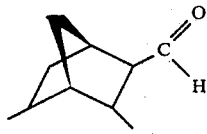

FIG. 7B represents the infra-red spectrum for peak 1 of the foregoing GLC profile consisting of the compound having the structure:

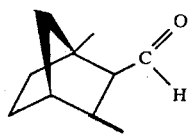

FIG. 8 represents the mass spectrum of the mixture of the foregoing distillation containing the compounds having the structures:

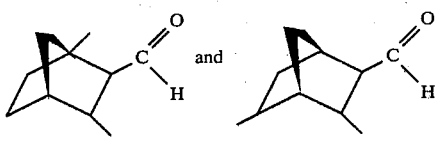

Both fractions 3 and 4 have a green, cut grass and minty aroma with fruity (apple) and herbaceous undertones.

Both fractions 3 and 4 have a eucalyptus, camphoraceous, blueberry-like, patchouli-like and fruity aroma profile and a camphoraceous, blueberry and patchouli-like flavor profile insofar as their use for foodstuffs is concerned. This causes them to be useful for blueberry and raspberry flavored foodstuffs.

EXAMPLE III

PREPARATION OF 1- AND 5-METHYL-5-NORBORNENE CARBOXALDEHYDE

Reaction:

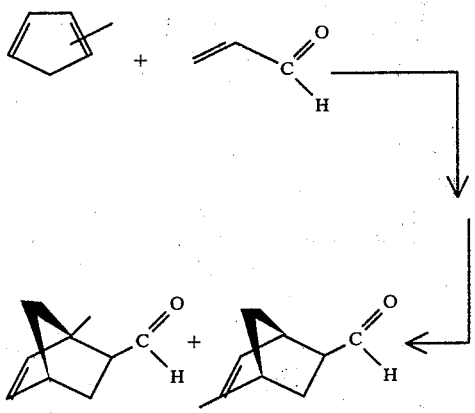

Into a 3-liter flask equipped with stirrer, thermometer, addition funnel, condenser, nitrogen purge, and cooling bath is charged 500 ml. Toluene and 50 grams of a 25% solution of ethyl aluminum dichloride. The resulting mixture is cooled to 20° C. and over a period of one hour while maintaining the temperature between 20° and 25° C., 280 grams of acrolein is added.

370 Grams of 1-methyl-1,3-cyclopentadiene and 2-methyl-1,3,cyclopentadiene produced according to Example A is mixed with 500 ml. Toluene. The resulting mixture is added over a period of two hours while maintaining the reaction temperature of 20°-22° C. to the reaction mass. The resulting reaction mass is then stirred at 21°-22° C. for a period of one hour. At the end of this period of time GLC analysis indicates that the reaction is complete.

The resulting reaction mass is poured into 1 kilogram of a 10% sodium chloride solution. The resulting mixture exists in two phases; an aqueous phase and an organic phase. The aqueous phase is removed and the organic phase is washed as follows:

A—one 250 ml. portion of 10% hydrochloric acid solution.
B—one 1 kilogram portion of 10% sodium chloride solution.
C—one 1 kilogram portion of 10% sodium hydroxide solution.
D—one 1 kilogram portion of 10% sodium chloride solution.
E—one 1 kilogram portion of 20% sodium chloride solution.

The toluene is stripped off of the reaction mass under reduced pressure.

Triethanolamine and 32 grams of Primol ® and 0.5 grams of Ionox ® and 0.5 grams of calcium carbonate is then added to the reaction mass and the reaction mass is distilled on a 12 inch Goodloe column yielding the following fractions:

| Fraction Number | Vapor Temp. (°C.) | Liquid Temp. (°C.) | Pressure (mm Hg) | Reflux Ratio | Weight of Fraction (gm) |
| --- | --- | --- | --- | --- | --- |
| 1 | 42 | 59 | 4.0 | 9:1 | 53.4 |
| 2 | 42 | 60 | 4.0 | 9:1 | 14.7 |
| 3 | 39 | 65 | 3.5 | 9:1 | 21.7 |
| 4 | 43 | 67 | 3.5 | 9:1 | 21.3 |
| 5 | 3 | 63 | 3.0 | 9:1 | 25.9 |
| 6 | 38 | 67 | 3.0 | 9:1 | 22.2 |
| 7 | 38 | 67 | 3.0 | 9:1 | 21.3 |
| 8 | 38 | 67 | 3.0 | 9:1 | 23.5 |
| 9 | 38 | 73 | 3.0 | 9:1 | 24.7 |
| 10 | 38 | 96 | 3.0 | 9:1 | 18.4 |
| 11 | 42 | 200 | 3.0 | 9:1 | 7.6 |

NMR, IR and mass spectral analysis yield the information that the reaction product consists of the two compounds having the structures:

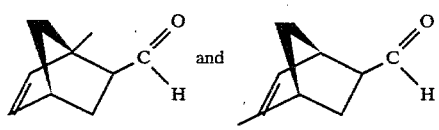

FIG. 9 represents the GLC profile after one hour of reaction.

FIG. 10A represents NMR spectrum for fraction 10 of the foregoing distillation, consisting of the compound having the structure:

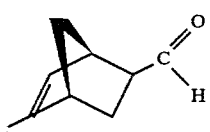

FIG. 10B represents the NMR spectrum for fraction 3 of the foregoing distillation, consisting of the compound having the structure:

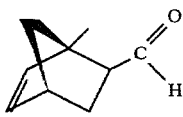

FIG. 11A represents the infra-red spectrum for fraction 10 of the foregoing distillation, consisting of the compound having the structure:

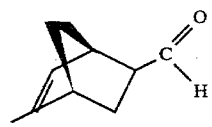

FIG. 11B represents the infra-red spectrum for fraction 3 of the foregoing distillation, consisting of the compound having the structure:

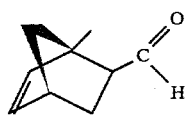

EXAMPLE IV

BASIC RASPBERRY FORMULATION

The following basic raspberry formulation is prepared:

| Ingredients | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

To a first portion of this basic formulation, a mixture of compounds having the structures:

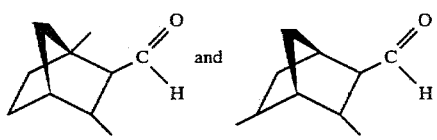

(produced according to Example II) has been added at the rate of 1%. Nothing is added to a second portion of this formulation. Both flavors with and without the compounds having the structures:

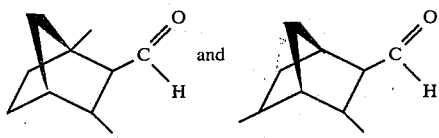

are compared at the rate of 100 parts per million by a bench panel of experts.

The flavor containing the compounds having the structures:

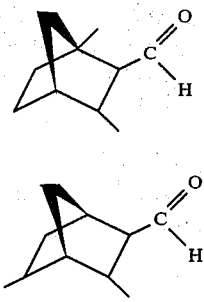

(Bulked fractions 3 and 4 of Example II) is considered to have a more raspberry kernel, more seedy herbaceous more natural character in both aroma and taste. The flavor is therefore preferred as more true to the taste of natural raspberries.

EXAMPLE V

The following mixture is prepared:

| Ingredients | Parts by Weight |
|---|---|
| Natural Raspberry Concentrate Juice | 2.5% |
| Water | 85.0% |
| Sugar syrup (37.5° Baume) | 12.5% |

The ripened raspberry and seedy, raspberry kernel note of this raspberry juice is imparted in increased strength by addition of a mixture of compounds having the structures:

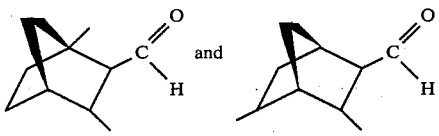

prepared according to Example II at the rate of from 0.02 ppm up to 10 ppm.

EXAMPLE VI

To the raspberry formulation as set forth in Example IV, the mixture of compounds having the structures:

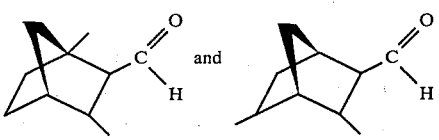

prepared according to Example II (Bulked fractions 3 and 4) is added at the rate of 0.2% this material is then called the "test composition". The raspberry formulation without the compounds having the structures:

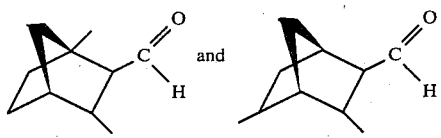

is called the "control composition".

The test and control compositions are added to the food products described hereinafter in the proportions shown for 10 kilograms of material to be flavored:

Pudding: 5-10 grams (0.15-0.1%)
Cooked sugar: 15-20 grams (0.15-2%)

Cooked sugar—100 ml of sugar syrup (prepared by dissolving 1 kilogram of sucrose in 600 ml of water) and 20 grams of glucose are mixed together and slowly heated to 145° C. The flavor is added and the mass is allowed to cool and harden.

Pudding—To 500 ml of warmed milk are added with stirring a mixture of 60 grams sucrose and 3 grams of pectin. The mixture is boiled for a few seconds and the flavor is added. The mixture is allowed to cool.

The finished foodstuff samples are tested by a panel of trained persons who express their views about the flavor of the samples. All members of the panel prefer the test samples having a more distinguished ripened raspberry aroma with taste of the ripe raspberries and its seedy kernel note.

An improved effect occurs when a mixture of 25:25:50 of 2-(4-hydroxy-4-methylpentyl)-norbornadiene: compound having the structure:

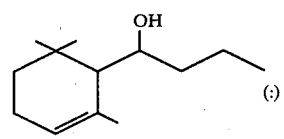

(:)

mixture of compounds produced according to Example II (Bulked fractions 3 and 4) having the structures:

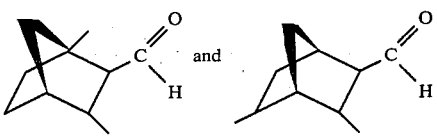

at the rate of 0.02 parts per million up to about 10 parts per million.

EXAMPLE VII

A. Powder Flavor Composition

20 Grams of the flavor composition of Example IV containing the compounds having the structures:

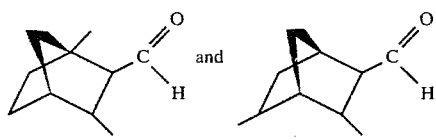

prepared according to Example II (Bulked fractions 3 and 4) is emulsified in a solution containing 300 grams gum acacia and 700 grams water. The emulsion is spray-dried with a Bowen Lab Model Drier utilizing 260 c.f.m. of air aith an inlet temperature of 500° F., an outlet temperature of 200° F., and a wheel speed of 50,000 rpm.

B. Sustained Release Flavor

The following mixture is prepared:

| Ingredients | Parts by Weight |
|---|---|
| Liquid Raspberry Flavor of Example IV | 20 |
| Propylene Glycol | 9 |
| Cab-O-Sil ® M-5 (Brand of Silica produced by the Cabot Corporation of 125 High Street Boston, Mass. 02112; Physical Properties: Surface area: 200 m$^2$/gm Nominal particle size: 0.012 microns Density: 2.3 lbs/cu.ft) | 5.00 |

The Cab-O-Sil is dispersed in the liquid raspberry flavor composition of Example IV with vigorous stirring, thereby resulting in a viscous liquid. 71 Parts by weight of the powder flavor composition of Part A, supra, is then blended into the said viscous liquid, with stirring at 25° C. for a period of thirty minutes resulting in a dry, free flowing sustained release raspberry flavor powder.

EXAMPLE VIII

10 Parts by weight of 5- Blook pigskin gelatin is added to 90 parts by weight of water at a temperature of 150° F. The mixture is agitated until the gelatin is completely dissolved and the solution is cooled to 120° F. 20 Parts by weight of the liquid raspberry flavor composition of Example IV is added to the solution which is then homogenized to form an emulsion having particle size typically in the range of 2–5 microns. This material is kept at 120° F. under which conditions the gelatin will not gel.

Coacervation is induced by adding, slowly and uniformly, 40 parts by weight of a 20% aqueous solution of sodium sulphate. During coacervartion the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting gelled coacervate may be filtered and washed with water at temperatures below the melting point of gelatin, to remove the salt.

EXAMPLE IX

Chewing Gum

100 Parts by weight of chicle are mixed with 4 parts by weight of the flavor prepared in accordance with Example VII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE X

Chewing Gum

100 Parts by weight of chicle are mixed with 18 parts by weight of the flavor prepared in accordance with Example VIII. 300 parts of sucrose and 100 parts of corn syrup are added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE XI

Toothpaste Formulation

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example VII |
| 100.00 (Total) | |

Procedure

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure yields a pleasant raspberry flavor, of constant strong intensity throughout said procedure (1–1.5 minutes).

EXAMPLE XII

Chewable Vitamin Tablets

The flavor material produced according to the process of Example VII is added to a Chewable Vitamin Tablet Formulation at the rate of 10 grams/kilogram which chewable vitamin tablet formulation is prepared as follows:

In as Hobart Mixer the following materials are blended to homogeneity:

|  | Gms/1000 tablets |
| --- | --- |
| Vitamin C (ascorbic acid) as ascorbic acid-sodium ascorbate mixture 1:1 | 70.00 |
| Vitamin B$_1$ (thiamine mononitrate) as Rocoat® thiamine mononitrate 33⅓% (Hoffman La Roche) | 4.0 |
| Vitamin B$_2$ (riboflavin) as Rocoat® riboflavin 33⅓% | 5.0 |
| Vitamin B (pyridoxine hydrochloride) as Rocoat® pyridoxine hydrochloride 33⅓% | 4.0 |
| Niacinamide as Rocoat® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry vitamin E acetate 33⅓% Roche |  |
| d-biotin | 6.6 |
| Flavor of Example VII | 0.004 (as indicated above) |
| Certified lake color | 5.0 |
| Sweetener - sodium saccharin | 1.0 |
| Magnesium stearate lubricant | 10.0 |
| Mannitol q.s. to make | 500.00 |

Preliminary tablets are prepared by slugging with flat-faced punches and grinding the slugs to 14 mesh. 13.5 g Dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong raspberry flavor for a period of 12 minutes.

EXAMPLE III

Chewing Tobacco

Onto 100 pounds of tobacco for chewing (85% Wisconsin leaf and 15% Pennsylvania leaf) the following casing is sprayed at a rate of 30%:

| Ingredients | Parts by Weight |
| --- | --- |
| Corn Syrup | 60 |
| Licorice | 10 |
| Glycerine | 20 |
| Fig Juice | 4.6 |
| Prune Juice | 5 |
| Flavor Material of Example VII | 0.4 |

The resultant product is redried to a moisture content of 20%. On chewing, this tobacco has an excellent substantially consistent, long lasting, licorice/raspberry flavor profile in conjunction with the tobacco note.

EXAMPLE XIV

Herbal Fragrance Produced Using Product Prepared According to Example II

The 1,3- and 3,5-dimethyl-5-norbornane carboxaldehyde

The following mixture is prepared:

| Ingredients | Relative Intensity |
| --- | --- |
| Amyl Cinnamic Aldehyde | 20% |
| Phenyl Acetaldehyde Dimethyl Acetal | 4% |
| Thyme Oil, White | 8% |
| Sauge Sclaree French | 8% |
| Galbanum Oil | 4% |
| Juniper Berry Oil | 10% |
| Methyl Octin Carbonate | 4% |
| Linalyl Acetate | 2% |
| Dihydro Methyl Jasmonate | 10% |
| Mixture of 1,3- and 3,5-Dimethyl-5-Norbornane Carboxaldehydes (prepared according to Example II) | 10% |

The mixture 1,3- and 3,5-dimethyl-2-norbornane carboxaldehydes prepared according to Example II (Bulked fractions 3 and 4) adds a strong green, cut grass and minty aroma with fruity herbaceous undertones to this herbal fragrance formulation causing it to be more "natural-like"

EXAMPLE XV

Preparation of a Detergent Composition

A granular detergent composition is prepared in accordance with Example IX of Canadian Pat. No. 1,004,566 containing the following ingredients:

| Ingredients | Weight % |
| --- | --- |
| Anhydrous Sodium Carbonate | 30.0 |
| Hydrated Sodium Silicate (81.5% solids, SiO$_2$:Na$_2$O ratio - 2.1:1 by weight) | 20.0 |
| Coconut Alcohol condensed with 6 molar proportions of ethylene oxide | 10.0 |
| Sodium citrate dihydrate | 10.0 |
| Sodium dichlorocyanurate dihydrate | 3.8 |
| Polyethylene glycol (available under the trademark Carbowax 4000;M.W. 3000–3700 | 2.0 |
| Dimethyl Silicone | 0.8 |
| Herbal Fragrance produced according to Example XIV | 5.9 |

This composition has an excellent herbaceous aroma with minty, cut grass nuances.

EXAMPLE XVI

Preparation of a Detergent Composition

A detergent is prepared from the following ingredients according to Example I of Canadian Pat. No. 1,007,948:

| Ingredients | Percent by Weight |
| --- | --- |
| "Neodol 45-11" (a C$_{14}$–C$_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 grams of the mixture of compounds according to Example II (Bulked fractions 3 and 4) having the structures:

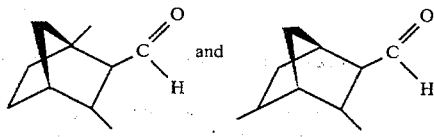

The resulting detergent has an excellent green cut grass and minty aroma with fruity and herbaceous undertones.

EXAMPLE XVII

Cologne and Handkerchief Perfume

One of the materials as set forth in Table I below is incorporated into Colognes at concentrations of 1.5%, 2.0%, 2.5%, 3.0%, 3.5% and 4.0% in 70%, 75%, 80%, 85%, 90% and 95% aqueous ethanol and into handkerchief perfumes at concentrations of 15%, 20%, 25% and 30% (in 75%, 80%, 85%, 90%, and 95% aqueous ethanol). In each of the cases distinct and definitive strong green, cut grass, minty, herbal fragrances with fruity undertones are imparted to the colognes and to the handkerchief perfumes:

TABLE I

A—Mixture of compounds prepared according to Example II (Bulked fractions 3 and 4) having the structures:

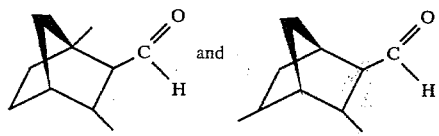

B—Compounds prepared according to Example Ii having the structure:

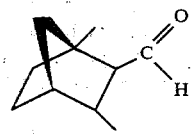

C—Compound prepared according to Example II having the structure:

D-Fragrance prepared according to Example XIV.

EXAMPLE XVIII

Liquid Detergent Composition

Concentrated liquid detergents with rich herbal nuances and minty undertones are prepared according to U.K. Pat. No. 1,526,942 containing 0.05%, 0.1%, 0.15% and 0.20% of the materials of Table II set forth below:

TABLE II

A—Mixture of compounds prepared according to Example II (Bulked fractions 3 and 4) having the structures:

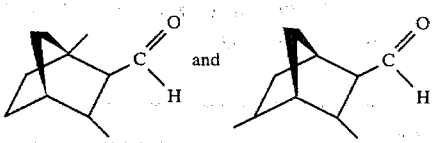

B—Compounds prepared according to Example II having the structure:

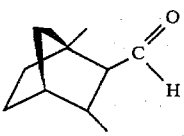

C—Compound prepared according to Example II having the structure:

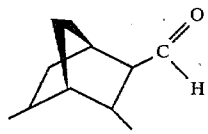

D—Fragrance prepared according to Example XIV.

They are prepared by adding and homogeneously admixing the appropriate quantity of substance of Table II in liquid detergent. Ther resulting detergents all posses intense herbal, green, cut grass-like and minty nuances with fruity undertones. The specific fragrances are each added to heavy duty liquid detergents formulated according to Example I on page 7 of United Kingdom Pat. No. 1,526,942 thusly:

| Ingredients | Weight % |
|---|---|
| Tallow alcohol (EO)$_{11}$ | 30 |
| Triethanolamine salt of linear alkyl benzene sulfonic acid wherein the alkyl chain averages 12 carbon atoms in length | 10 |
| Condensation product of average 4 moles of ethylene oxide with $C_{14}$–$C_{15}$ alcohol | 10 |
| Butanol | 15 |
| Brightener (Optical Brightening Agent) | 0.25 |
| Water | Balance |

Each of the compositions prepared with each of the substances of Table II is stable and provides excellent fabric cleaning when used either full-strength as a pretreatment or through the wash detergency at a level of 6,000 ppm. In addition the above composition gives superior cleaning of greasy cosmetic stains and furthermore, on cleaning the aroma of the detergent has a faint

EXAMPLE XX

Fabric Conditioning Substance

According to Example I of U.K. Pat. No. 1,544,863 a pre-soaking/wash additive composition of the following formulation is prepared:

| Component | Weight % |
|---|---|
| Sodium Perborate Tetrahydrate | 5 |
| Sodium Tripolyphosphate | 30 |
| Borax | 17 |
| Tallow Alcohol Ethoxylate | 1 |
| Spray-Dried Detergent Granules | 28 |
| Enzyme | 0.3 |
| Fabric Conditioning Prills (Average Prill Size = 75 microns) | 15.3 percent |
| Commercial Sorbitan Tristearate | 10.0 |
| Ditallow Dimethyl Ammonium Methylsulfate | |
| A perfume substance as set forth in Table III thusly: | 5.0 |

TABLE III

A—Mixture of compounds prepared according to Example II (Bulked fractions 3 and 4) having the structures:

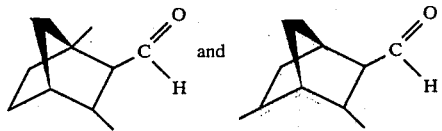

B—Compounds prepared according to Example II having the structure:

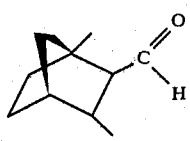

C—Compound prepared according to Example II having the structure:

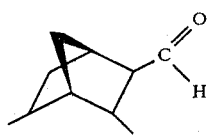

D—Fragrance prepared according to Example XIV.

The composition is prepared by dry mixing the requisite granular ingredients until a homogeneous granular product having a melting or softening point of from 35°–58° C. is secured.

The composition is (a half cup) added to a conventional 17–19 gallon automatic washing machine in along with soiled articles of clothing and one cup of a commercial anionic detergent product. Thereafter the articles are laundered in the machine in a conventional manner for ten minutes in wash water of 40° C. The clothing articles are then rinsed, spin dryed in the automatic washing machine and are thereafter placed in an automatic laundry dryer. The dryer is operated at an average temperature of 50° C. for a period of 40 minutes. Upon removal of the fabrics from the dryer clothing articles are perceived to have a soft feel and a noticeable herbaceous, perfume aroma from the wash additive composition perfume.

What is claimed is:

1. A process for augmenting or enhancing the aroma or taste of a foodstuff comprising the step of adding to a foodstuff from 0.05 parts per million up to about 300 parts per million based on the foodstuff of at least one methyl substituted norbornane carboxaldehyde derivative defined according to the structure:

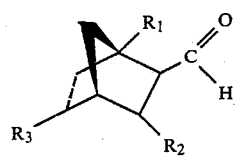

wherein the dashed line represents a carbon-carbon single bond or a carbon-carbon double bond; and wherein $R_1$, $R_2$ and $R_3$ are each selected from the group consisting of methyl and hydrogen with the proviso (i) when $R_1$ is hydrogen, $R_2$ is methyl and (ii) when $R_1$ is methyl, $R_3$ is hydrogen.

2. The process of claim 1 wherein the norbornane carboxaldehyde derivative is a mixture of compounds having the structures:

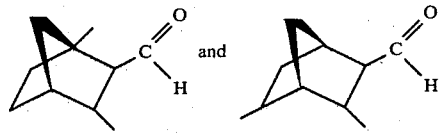

* * * * *